(12) United States Patent
de Charmoy Grey et al.

(10) Patent No.: US 6,575,020 B1
(45) Date of Patent: Jun. 10, 2003

(54) TRANSDUCER FOR MICROFLUID HANDLING SYSTEM

(75) Inventors: Hasin Francois de Charmoy Grey, Copenhagen (DK); Tove Maria Henriette Jensenius, Copenhagen (DK); Jacob Thaysen, Copenhagen (DK); Anja Boisen, Valby (DK)

(73) Assignee: Cantion A/S, Broendby (DK)

( * ) Notice: Subject to any disclaimer, the term of this patent is extended or adjusted under 35 U.S.C. 154(b) by 0 days.

(21) Appl. No.: 09/563,331

(22) Filed: May 3, 2000

Related U.S. Application Data
(60) Provisional application No. 60/133,240, filed on May 7, 1999.

(30) Foreign Application Priority Data

May 3, 1999 (DK) .......................................... 1999 00601

(51) Int. Cl.[7] ........................ G01N 11/00; G01N 33/20
(52) U.S. Cl. .................... 73/54.23; 73/53.01; 73/54.24; 73/54.25; 73/61.45
(58) Field of Search ............................ 73/24.06, 31.06, 73/53.01, 54.23, 54.24, 54.25, 54.26, 54.27, 54.38, 54.41, 54.42, 61.45, 61.61, 61.78, 61.79

(56) References Cited

U.S. PATENT DOCUMENTS

| | | | | |
|---|---|---|---|---|
| 4,549,427 A | * | 10/1985 | Kolesar, Jr. ................. | 73/24.01 |
| 4,674,319 A | * | 6/1987 | Muller et al. ............... | 73/24.01 |
| 4,789,804 A | * | 12/1988 | Karube et al. ............... | 310/311 |
| 5,698,931 A | * | 12/1997 | Shibata et al. ............... | 310/327 |
| 5,719,324 A | | 2/1998 | Thundat et al. ............. | 73/24.01 |
| 5,807,758 A | | 9/1998 | Lee et al. ................... | 436/526 |
| 5,819,749 A | * | 10/1998 | Lee et al. ................... | 128/899 |
| 5,892,143 A | * | 4/1999 | Namerikawa et al. ..... | 73/54.24 |
| 6,016,686 A | * | 1/2000 | Thundat ..................... | 73/24.06 |
| 6,073,482 A | * | 7/2000 | Moles ........................ | 73/53.01 |

(List continued on next page.)

FOREIGN PATENT DOCUMENTS

| | | | | |
|---|---|---|---|---|
| EP | 072744 A2 | | 2/1983 | |
| JP | 06273303 A | * | 9/1994 | ............... 73/19.03 |
| WO | WO 9938007 | | 7/1999 | |

OTHER PUBLICATIONS

L.P. Lee et al., "Key Elements of Transparent Teflon® Microfluidic System," Berkeley Sensor & Actuator Center, pp. 245–248.

L.P. Lee et al., "High aspect ratio polymer microstructures and cantilevers for bioMEMS usinglow energy ion beam and photolitography," Sensors and Actuators A 71 (1998) pp. 144–149.

(List continued on next page.)

*Primary Examiner*—Daniel S. Larkin
*Assistant Examiner*—Michael Cygan
(74) *Attorney, Agent, or Firm*—Birch, Stewart, Kolasch & Birch, LLP

(57) ABSTRACT

The present invention relates to integrated micro-cantilevers, micro-bridges or micro-membranes in micro-liquid handling systems. Such micro-liquid handling systems provide novel detection mechanisms for monitoring the physical, chemical and biological properties of fluids in such systems. The present invention further relates to micro-cantilever, micro-bridge or micro-membrane type sensors having integrated readout. Such constructions allow laminated flows of different liquids to flow in a channel without mixing, which opens up for new type of experiments and which reduces noise related to the liquid movement. The present invention even further relates to sensors having adjacent or very closely spaced micro-cantilevers, micro-bridges or micro-membranes which can be exposed to different chemical environments at the same time.

88 Claims, 15 Drawing Sheets

U.S. PATENT DOCUMENTS

| | | | |
|---|---|---|---|
| 6,167,748 B1 * | 1/2001 | Britton, Jr. et al. | 73/24.06 |
| 6,201,980 B1 * | 3/2001 | Darrow et al. | 600/345 |
| 6,203,983 B1 | 3/2001 | Quate et al. | |
| 6,303,288 B1 * | 10/2001 | Furcht et al. | 422/56 |
| 6,436,647 B1 | 8/2002 | Quate et al. | |

OTHER PUBLICATIONS

D. R. Baselt et al., "A High–Sensitivity Micromachined Biosensor," Proceedings of the IEEE, vol. 85, No. 4, Apr. 1997, pp. 672–679.

S.J. O'Shea et al., "Atomic force microscopy stress sensors for studies in liquids," J. Vac. Sci. Technol. B 14(2), Mar./Apr. 1996, pp. 1383–1385.

R. Berger et al., "Thermal analysis using a micromechanical calorimeter," Appl. Phys. Lett. 69 (1), Jul. 1996, pp. 40–42.

R. Berger et al., "Surface Stress in the Self–Assembly of Alkanethiols on Gold," Science vol. 276, Jun. 1997, pp. 1942, 1945, 2021–2024.

R. Raiteri et al., "Measuring Electrochemically Induced Surface Stress with an Atomic Force Microscope," J. Phys. Chem., vol. 99, No. 43, 1995, pp. 15728–15732.

R. Berger et al., Micromechanics: A Toolbox for Femtoscale Science: "Towards a Laboratory on a Tip", Elsevier Science 1997, Microelectronic Engineering 35, pp. 373–379.

J.K. Gimzewski et al., "Observation of a chemcal reaction using a micromechanical sensor," Chemical Physics Letters, Jan. 1994, vol. 217, Nos. 5,6, pp. 589–594.

J.P. Cleveland et al., "A nondestructive method for determining the spring constant of cantilevers for scanning force microscopy," Rev. Sci. Instrum., 64 (2) Feb. 1993, pp. 403–405.

Jianming Chen, "Sub–Nanogram Mass Sensor for In–Liquid Measurement," Ph.D. Thesis, Simon Fraser University, Dec. 1995.

* cited by examiner

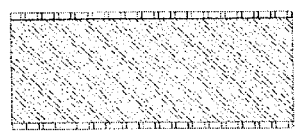
a) Thermal oxidation
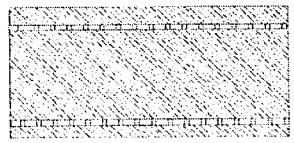
b) Deposition of LPCVD a-Si
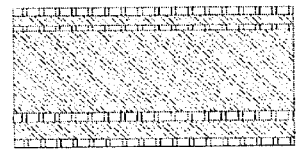
c) Thermal oxidation
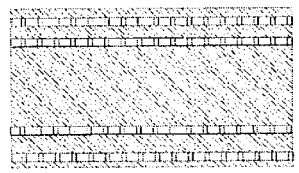
d) Deposition of LPCVD a-Si
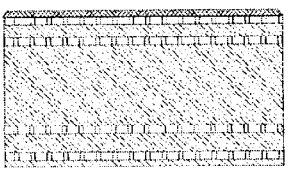
e) Boron implantation
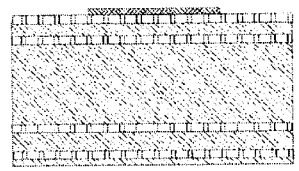
f) RIE of resistor
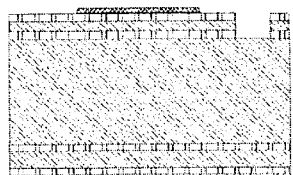
g) RIE etch of cantilever
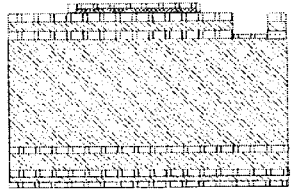
h) Thermal oxidation
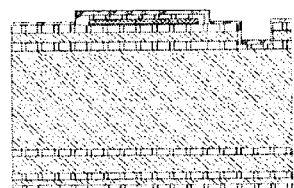
i) Thin LPCVD nitride
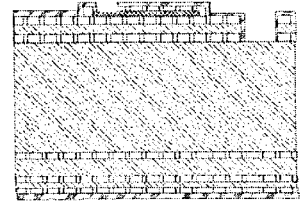
j) RIE of nitride for contact+ HF etch of oxide
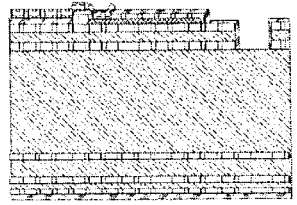
k) Metal for electrical connections
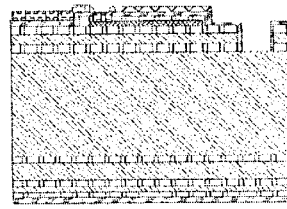
l) Metal for immobilisation
oxide  silicon (100)  nitride  silicon p  metal  Imm-Metal
Fig. 5 silicon (100)   nitride   metal   Imm-Metal

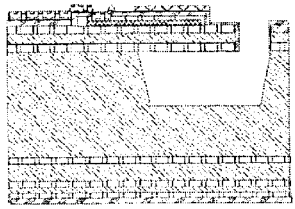
a) KOH etch of channel

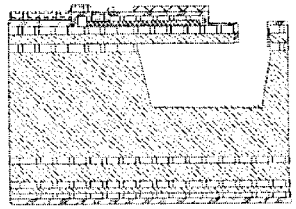
b) HF etch of cantilever oxide

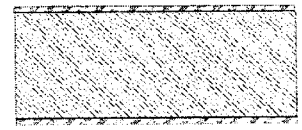
c) Deposition of LPCVD nitride on new wafer

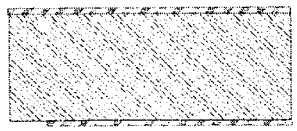
d) Pattering back side for KOH etch of contact hole

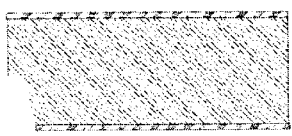
e) KOH etch of contact holet

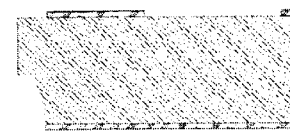
f) Patterning front side for KOH etch of channel

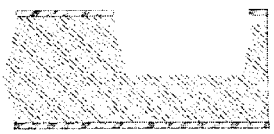
g) KOH etch of channel and contact hole

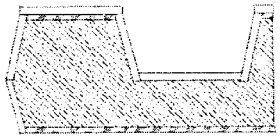
h) Evaporation of glass

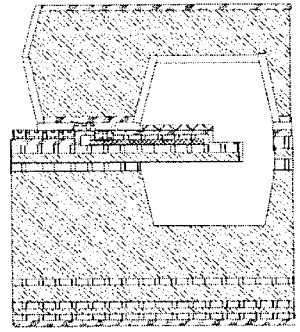
i) Anodic bonding and Hf of oxide oxide ▨ silicon (100) ▨ nitride ▨ silicon p ▨ metal ▨ Imm-Metal ▨ glass

Fig. 9

TRANSDUCER FOR MICROFLUID HANDLING SYSTEM

This Application claims the benefit of No. 60/133,240, filed May 7, 1999.

FIELD OF THE INVENTION

The present invention relates to a sensor using microscopic flexible mechanical structures such as micro-cantilevers, micro-bridges or micro-membranes integrated into microscopic chambers. In particular, the present invention relates to a sensor for measuring biochemical properties of fluids in such chambers.

TECHNICAL BACKGROUND

The measurement of the properties of fluids flowing in microscopic channels is of importance in the field of micro liquid handling systems, which includes systems for measuring:

1) physical properties such as flow rates viscosity and local temperature
2) chemical properties such as pH and chemical composition
3) biological properties such as identification of organic constituents in fluids, including DNA fragments, proteins, and complete biological cells Microliquid handling systems typically consist of narrow channels of order 100 microns wide and 100 microns deep engraved or embossed into the surface of a thin wafer of a material such as silicon, glass or plastic using reproduction techniques based on micromachining. The surface containing the channels is usually bonded to another surface, in order to seal the channels. Fluids pumped through the resulting channels typically flow in a completely laminar fashion. As a result, several different fluids can be flowed in laminated streams through such microsystems, without any significant mixing of the fluids.

An important advantage of a microliquid handling system is that very small quantities of fluid can be directed in a controlled fashion to various parts of the system, where various analytical techniques can be used to determine the properties of the liquid. This can be done using external analytical techniques such as optical detection. The controlled flow of the fluid is achieved via pumps and valve systems that can be either external or integrated with the microchannels.

Micro-cantilevers are devices where changes in the mechanical properties of a microscopic micro-cantilever are used to detect changes in the environment of the micro-cantilever. The micro-cantilever is typically of the order of 100 microns long, 10 microns wide and one micron thick. The micro-cantilevers are made of a material such as silicon, silicon nitride, glass, metal or combination of any of these, using micromachining techniques. A change in the mechanical properties can for example be a stress formation in the micro-cantilever due to changes in surface stress of the micro-cantilever. Stress formation can also occur due to changes in temperature of the micro-cantilever due to a bimorph effect, if the micro-cantilever is made of two materials with different thermal expansion coefficients. Such stress formations in the micro-cantilever can be detected in a variety of ways. Often the stress formation will result in a deflection of the micro-cantilever. In these situations the deflection can be detected by deflection of a laser light beam by a reflecting surface of the micro-cantilever. Change in the resistivity of a piezoresistor integrated onto the micro-cantilever is another method, which has the advantage that it does not depend on a deflection of the micro-cantilever and it does not require optical access to the micro-antilever.

Change in resonance frequency is another example of a change in a mechanical property. A change in mass of the micro-cantilever can occur if material binds to the micro-cantilever, and such a change will produce a change in the resonance frequency of the micro-cantilever. Such changes can be monitored by actuating the micro-cantilever at a frequency near its resonance frequency, and monitoring changes in the amplitude of the resulting dynamic bending of the micro-cantilever, using methods similar to those described above for the detection of stress formation.

Using these changes in mechanical properties, micro-cantilevers, have been used to detect chemical reactions occurring on the surface of the micro-cantilever, either in gas phase or in liquid phase. For gas phase experiments the measurements have been performed in a gas chamber utilizing optical detection of a micro-cantilever bending. Micro-cantilevers with integrated piezoresistive read-out have been used for thermogravimetry in air. Under ambient conditions the micro-cantilever-based detection technique has proven very sensitive. It has been demonstrated that mass changes down to 0.5 ng and temperature changes down to approximately $10^{-5}$ C can be resolved. Furthermore, a change of surface stress on the order of $10^{-5}$ N/m has been detected. In liquids, J. Chen [J. Chen, Ph.D thesis Simon Fraser University (1995)] reports on a piezoresistive micro-cantilever for mass change detection. Detection of polystyrene spheres was performed in a 3 water tank in which the micro-cantilever was placed. By vibrating the micro-cantilever, changes in the resonance frequency and thereby mass changes of the micro-cantilever could be monitored. The micro-cantilever deflection was monitored by integrated piezoresistive read-out.

PCT patent application WO99/38007 published Jul. 29 1999 describes a system for detecting analytes in a fluid using functionalised micro-cantilevers mounted in a tube. A bending of the micro-cantilever is induced by molecular interactions on one side of the micro-cantilever. The bending is monitored optically by the reflection of a laser beam of the end of the micro-cantilever. Examples of application include the formation of self assembled monolayers (SAM's) of alkylthiols on a goldcoated micro-cantilever and the partially reversible adsorption of low density lipoproteins. The possibility of testing multiple analytes against multiple analytes is mentioned. A solution for generating a reference signal is proposed exploiting the twisting movement of the micro-cantilever and the ability to distinguish the twisting from the bending movement. Low flow rates are recommended in order to avoid perturbations of the micro-cantilever. This is a clear indication that the envisioned flow system is of macroscopic dimensions.

A micro-cantilever array placed at the top of an open channel has been realised in polymer [C. P. Lee et al., Prooceeding of the $\mu$TAS'98 workshop (1998) 245–252; L. P. Lang et al., Sensors and Actuators A 71 (1998) 144–149]. C. P Lee et al. suggest that these micro-cantilevers can be modified for the use of biochemically functionalized tips for use in atomic force microscopy (AFM) or in scanning near field microscopy (SNOM). Hence, this proposed application is related to surface imaging.

Commercially available micro-cantilevers have been used as sensors in liquid. D. R. Baselt et al.[D. R. Baselt et al.,Proceedings of the IEEE. Vol. 85 4 (1997) 672–679] report on piezoresistive micro-cantilevers applied as biosensors using magnetic particles. The coated micro-cantilevers are placed in a liquid cell in which the detection takes place. The micro-cantilevers measure the interaction between particles immobilised on magnetic beads and the immobilised particles on the micro-cantilever surface. If the magnetic beads bind to the surface, the application of a large magnetic field will cause a bending of the micro-cantilever.

U.S. Pat. No. 5,719,324 describes a micro-cantilever based sensor, where a mass change of the micro-cantilever is detected as a change in the resonance frequency of the micro-cantilever. Furthermore, a stress change of a micro-cantilever material is monitored as a micro-cantilever deflection. For mass detection, a piezoelectric actuator oscillates the micro-cantilever and the micro-cantilever deflection is registered by optical read-out. It is mentioned that the mass detection principle can also be applied in liquid.

It is a disadvantage of the above-mentioned systems that micro-cantilever based experiments are carried out in large liquid containers. Such large liquid container systems are very difficult to stabilise thermally. Furthermore, in such large container systems the required volume of chemicals is unnecessary high.

It is a further disadvantage of most of the above-mentioned systems that the micro-cantilever deflection is detected optically. This disadvantage is due to the fact that it may be difficult to obtain optical access to a specific micro-cantilever—especially in the case where a plurality of micro-cantilevers are closely spaced and in the case where the liquid is not transparent.

It is an object of the present invention to integrate micro-cantilevers, micro-bridges or micro-membranes into closed micro-liquid handling systems, in order to provide novel detection mechanisms for monitoring the physical, chemical and biological properties of fluids in such systems.

It is a still further object of the present invention to provide a micro-cantilever, micro-bridge or micro-membrane type sensor having integrated readout. A closed micro-liquid handling system allows laminated flows of different liquids to flow in the channel without mixing, which opens up for new type of experiments and which reduces noise related to the liquid movement.

It is a still further object of the present invention to provide adjacent or very closely spaced micro-cantilevers, micro-bridges or micro-membranes which can be exposed to different chemical environments at the same time by:

Laminating the fluid flow vertically in the micro-channel into two or more streams, so that micro-cantilevers or micro-membranes on opposing sides of the micro-channel are immersed in different fluids, or so that a micro-cantilever, micro-bridge, or micro-membrane is exposed to two different fluids.

Laminating the fluid flow horizontally in the micro-channel, so that micro-cantilevers or micro-bridges recessed to different levels in the micro-channel or micro-membranes placed at the top and at the bottom of the channel are exposed to different fluids.

In this way, changes in viscous drag, surface stress, temperature, or resonance properties of adjacent or closely spaced micro-cantilevers, micro-bridges or micro-membranes induced by their different fluid environments, can be compared.

Neighbouring or very closely spaced micro-cantilevers, micro-bridges or micro-membranes can be coated with different chemical substances using the method just described for immersing adjacent or neighbouring micro-cantilevers, micro-bridges or micro-membranes in different fluids. After coating, the micro-channels can be flushed with other fluids to remove the coating material, and to compare the reactivity of neighbouring or very closely spaced micro-cantilevers, micro-bridges or micro-membranes with different coatings.

It is a still further object of the present invention to provide a micro-cantilever, micro-bridge or micro-membrane based sensor where the liquid volume is minimised in order to reduce the use of chemicals and in order to obtain a system which is easy to stabilise thermally.

SUMMARY OF THE INVENTION

The above-mentioned objects are complied with by providing, in a first aspect, a sensor for detecting the presence of a substance in a fluid, said sensor comprising:

means for handling the fluid, said handling means comprising an interaction chamber of micrometer dimensions, an inlet and an outlet, a first flexible member having a surface, said surface holding a substance, wherein the surface holding the substance is at least partly positioned inside the interaction chamber so that at least part of the substance is exposed to the fluid, and means for detecting a mechanical parameter associated with the first flexible member, said mechanical parameter being related to the presence of the substance in the fluid.

By micrometer dimension is meant that the interaction chamber has dimensions in the 50–500 microns range (width and depth). The first flexible member may comprise a micro-cantilever having a first and a second end, the first end being attached to the interaction chamber. The micro-cantilever may have a rectangular form and may be approximately 50 $\mu$m wide, 200 $\mu$m long and 1 $\mu$m thick.

The mechanical parameter being associated with the first flexible member may both be a static or dynamic parameter. By static is meant that the flexible member may be subject to a static deformation—e.g. bending. Static deformations are typically induced by stress changes in the flexible member. By dynamic is meant the flexible member may be driven at or near its mechanical resonance frequency. Upon detection of a substance in the fluid the resonance frequency may chance due to a change of mass of the flexible member.

Alternatively, the first flexible member may comprise a micro-bridge having a first and a second end, wherein the first and second ends are attached to the interaction chamber. The dimensions (wide, length and thickness) of a micro-bridge may be similar to the dimensions of the micro-cantilever. Alternatively, the first flexible member may form part of a boundary defining the interaction chamber. The boundary may here be one of the sidewalls of the interaction chamber.

The detecting means for detecting the mechanical parameter associated with the first flexible member may comprise a piezoresistive element, preferably being an integral part of the first flexible member. Preferably, the piezoresistive element forms part of a balanced bridge, such as a Wheatstone bridge. Alternatively, the detecting means may comprise a laser, an optical element and a position sensitive photo detector.

The sensor according to the first aspect of the present invention may further comprise an actuator for moving the flexible member relative to the interaction chamber. The actuator may be implemented in several ways—e.g. by comprising piezoelectric elements, comprising means for providing an electrostatic induced movement, comprising means for providing a magnetic induced movement, or by comprising means for providing a thermal induced movement.

The handling means may be fabricated in a material selected from the group consisting of metals, glasses, polymers or semiconductor materials, such as silicon.

The substance being held by the surface of the first flexible member may be selected from the group consisting of metals, polymers, biochemical molecules or micro-biochemical structures. The group of biochemical molecules and micro-biochemical structures comprises enzymes, DNA, Cells and proteins.

The sensor according to the first aspect of the invention may further comprise a second flexible member being at least partly positioned inside the interaction chamber so that at least part of the second flexible member is exposed to the fluid The sensor may further comprise means for detecting a mechanical parameter associated with the second flexible member. This detecting means may comprise a piezoresistive element being an integral part of the second flexible member. The piezoresistive element may form part of a balanced bridge, such as a Wheatstone bridge.

The second flexible member may serve as a reference to the first flexible member and thereby being adapted to generate a reference signal via the detecting means.

In a second aspect, the present invention relates to a sensor for detecting the presence of a substance in a fluid, said sensor comprising:

means for handling the fluid, said handling means comprising an interaction chamber, an inlet and an outlet, a first flexible member having a surface, said surface holding a substance, wherein the surface holding the substance is at least partly positioned inside the interaction chamber so that at least part of the substance is exposed to the fluid, and means for detecting a mechanical parameter associated with the first flexible member, said mechanical parameter being related to the presence of the substance in the fluid, wherein the detecting means form an integral part of the first flexible member.

The first flexible member, the detecting means, the actuator may be implemented as previously mentioned. The interaction chamber may be of micrometer dimensions—i.e. the 50–500 μm range.

The handling means may be fabricated in a material selected from the group consisting of metals, glasses, polymers or semiconductor materials, such as silicon. The substance being held by the surface of the first flexible member may be selected from the group consisting of metals, polymers, biochemical molecules or micro-biochemical structures. The group of biochemical molecules and micro-biochemical structures comprises enzymes, DNA, Cells and proteins.

In order to obtain a reference signal the sensor according to the second aspect may further comprise a second flexible member being at least partly positioned inside the interaction chamber so that at least part of the second flexible member is exposed to the fluid, and means for detecting a mechanical parameter associated with the second flexible member.

Also here the detecting means may comprise a piezoresistive element, said piezoresistive element being an integral part of the second flexible member, and wherein the piezoresistive element forms part of a balanced bridge, such as a Wheatstone bridge.

In a third aspect, the present invention relates to a sensor for detecting the presence of a substance in a fluid, said sensor comprising:

means for handling the fluid, said handling means comprising an interaction chamber, an inlet and an outlet, a first flexible member having a surface, said surface holding a substance, wherein the surface holding the substance is at least partly positioned inside the interaction chamber so that at least part of the substance is exposed to the fluid, and wherein the first flexible member forms an integral part of the handling means, and means for detecting a mechanical parameter associated with the first flexible member, said mechanical parameter being related to the presence of the substance in the fluid.

That the flexible member forms an integral part of the handling also means that the flexible member may be fabricated separately and then afterwards being attached to the handling means using a plug-on or snap-on solution. The handling and flexible member may then afterwards be encapsulated to form at least part of the final sensor.

Again, the first flexible member, the detecting means, and the actuator may be implemented as previously described. Also suitable materials for fabrication of the handling means and suitable substances have previously been described.

Furthermore, the detecting means for detecting the mechanical parameter associated with the first flexible member may comprise a laser, an optical element and a position sensitive photo detector.

A reference signal may be generated by a second flexible member being at least partly positioned inside the interaction chamber so that at least part of the second flexible member is exposed to the fluid. The reference signal itself may be generated by a detecting means for detecting a mechanical parameter associated with the second flexible member. The detecting means may comprise a piezoresistive element, said piezoresistive element being an integral part of the second flexible member, and wherein the piezoresistive element forms part of a balanced bridge, such as a Wheatstone bridge.

In a fourth aspect, the present invention relates to a sensor for detecting the presence of a substance in a fluid, said sensor comprising:

means for handling the fluid, said handling means comprising an interaction chamber, an inlet and an outlet, a first flexible member having a surface, said surface holding a substance, wherein the surface holding the substance is at least partly positioned inside the interaction chamber so that at least part of the substance is exposed to the fluid, and wherein fabrication of the first flexible member is part of fabrication of the handling means, means for detecting a mechanical parameter associated with the first flexible member, said mechanical parameter being related to the presence of the substance in the fluid.

The fact that the fabrication of the first flexible member is part of the fabrication of the handling means is to be understood in the following way. The fabrication of the handling means involves a plurality of steps. One or more of these step may involve the fabrication of the first flexible member. This issue is addressed in further details in "Detailed description of the invention".

The first flexible member, the detecting means, and the actuator may be implemented as previously described. Also suitable materials for fabrication of the handling means and suitable substances have previously been described. Also according to this aspect, the sensor may further comprise a second flexible member being at least partly positioned inside the interaction chamber so that at least part of the second flexible member is exposed to the fluid, and means for detecting a mechanical parameter associated with the second flexible member.

In a fifth aspect, the present invention relates to a sensor for detecting the presence of a first and a second substance in a fluid, said sensor comprising:

means for handling the fluid, said handling means comprising an interaction chamber of micrometer dimensions, an inlet and an outlet, a first flexible member having a surface, said surface holding a first substance, wherein the surface holding the first substance is at least partly positioned inside the interaction chamber so that at least part of the first substance is exposed to the fluid, a second flexible member having a surface, said surface holding a second substance, wherein the surface holding the second substance is at least partly positioned inside the interaction chamber so that at least part of the second substance is exposed to the fluid, a first detecting means for detecting a first mechanical parameter associated with the first flexible member, said first mechanical parameter being related to the presence of the first substance in the fluid, and a second detecting means for detecting a second mechanical parameter associated with the second flexible member, said second mechanical parameter being related to the presence of the second substance in the fluid.

The first and second flexible members may comprise a micro-cantilever having a first and a second end, wherein the first end is attached to the interaction chamber. Alternatively, the first and second flexible members may comprise a micro-bridge having a first and a second end, wherein the first and second ends are attached to the interaction chamber. Finally, each of the first and second flexible members may form part of a boundary defining the interaction chamber. This boundary may be a sidewall of the interaction chamber.

The detecting means may comprise piezoresistive elements being integral parts of the first flexible member. The detecting means may also comprise lasers, optical elements and a position sensitive photo detectors.

The sensor may further comprise actuators for the flexible members. These actuators may comprise piezoelectric elements being integral parts of the micro-cantilevers. Other types of actuators may also be applied.

The handling means may be fabricated in a material selected from the group consisting of metals, glasses, polymers or semiconductor materials, such as silicon. The substances being held by the surface of the first and second flexible members may be selected from the group consisting of metals, polymers, biochemical molecules or micro-biochemical structures. The group of biochemical molecules and micro-biochemical structures comprises enzymes, DNA, Cells and proteins.

In a sixth and final aspect, the present invention relates to a sensor for detecting the presence of a first and a second substance in a moving laminated fluid, said laminated fluid comprising, in a cross section perpendicular to a direction of movement, a first and a second region, said sensor comprising:

means for handling the laminated fluid, said handling means comprising an interaction chamber, an inlet and an outlet, a first flexible member having a surface, said surface holding a first substance, wherein the surface holding the first substance is at least partly positioned inside the interaction chamber so that at least part of the first substance is exposed to the first region of the laminated fluid, a second flexible member having a surface, said surface holding a second substance, wherein the surface holding the second substance is at least partly positioned inside the interaction chamber so that at least part of the second substance is exposed to the second region of the laminated fluid, means for detecting a first mechanical parameter associated with the first flexible member, said first mechanical parameter being related to the presence of the first substance in the first region of the fluid, and means for detecting a second mechanical parameter associated with the second flexible member, said second mechanical parameter being related to the presence of the second substance in the second region of the fluid.

By a moving laminated flow is meant that a measurements may be performed in a continues liquid flow or, alternatively, that the liquid is introduced into the chamber and then temporarily stopped while the measurements are being performed. After the measurements have been performed the liquid is guided away from the chamber.

The detecting means for detecting the mechanical parameters associated with the first and second flexible members may comprise piezoresistive elements being integral parts of the flexible members. Alternatively, the detecting means for detecting the first and second mechanical parameters associated with the first and second flexible member, may comprise lasers, optical elements and a position sensitive photo detectors.

Furthermore actuators may be applied for moving part of the flexible elements relative to the handling means. These actuators may comprise piezoelectric elements, said piezoelectric elements being integral parts of the flexible members. Also with regard to this aspect, the handling means may be fabricated in a material selected from the group consisting of metals, glasses, polymers or semiconductor materials, such as silicon. The substances to by held be the flexible members may be as previously mentioned.

It is an advantage of the present invention that piezoresistors are integrated and used to measure the deflections of the flexible members.

It is a still further advantage of the present invention that a plurality flexible members can be integrated closely together in a micro-system, so that one flexible member can serve as a reference to another, or that nearby flexible members can be immersed in different laminated streams in a fluid flow, so that one fluid can serve as a reference to another.

It is a still further advantage of the present invention that it provides a sensor where the liquid volume is minimised in order to reduce the use of chemicals and in order to obtain a system which is easy to stabilise thermally.

The above object, advantages and features, together with numerous other advantages and features will be evident from the detailed description below of preferred embodiments of the present invention.

BRIEF DESCRIPTION OF THE DRAWINGS

FIG. 5: Schematic cross-sectional view of the process sequence of the lower part of the channel and the micro-cantilever.

FIG. 9: Schematic cross-sectional view of the process sequence of the upper part of the channel. The channel is defined by the use of anodic bonding.

DETAILED DESCRIPTION OF THE INVENTION

Figure 1:
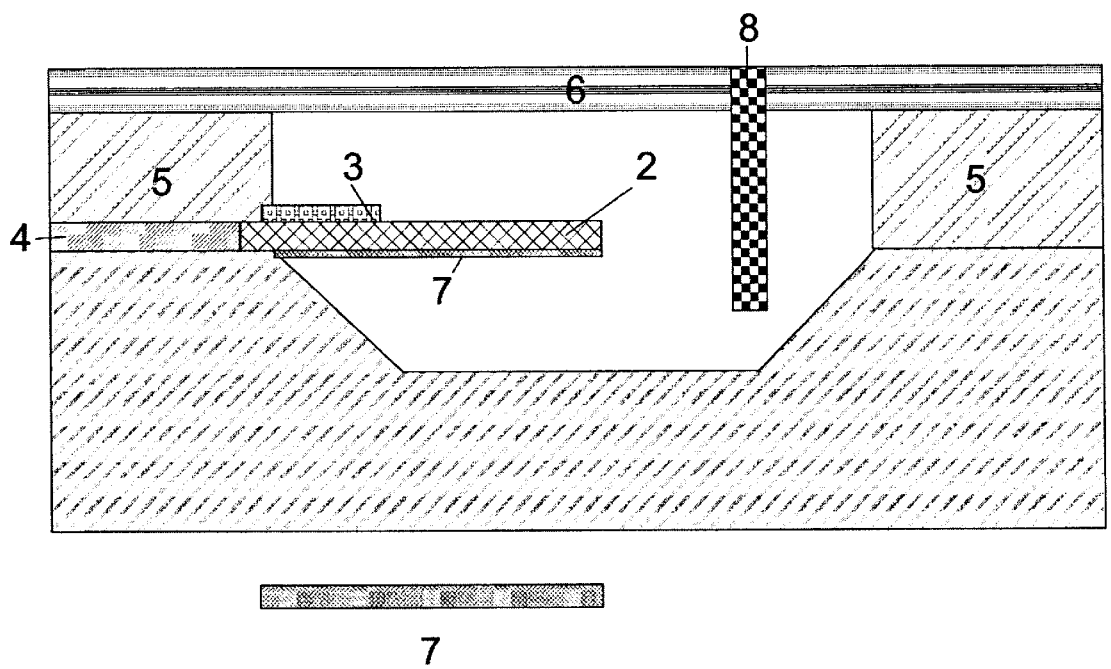
FIG. 1: Schematic cross-sectional view of a micro-channel with integrated micro-cantilever.

Micrometer-sized mechanical structures such as micro-cantilevers, micro-bridges and micro-membranes can be used as very sensitive sensors in environments ranging from cryogenic temperatures and ultra-high vacuum to ambient conditions and physiological liquids. Especially the latter makes it interesting for biochemical applications.

Basically, a biochemical reaction at a micro-cantilever, micro-bridge or micro-membrane surface can result in a temperature change or in a change in the surface stress. The temperature change is observed by coating the microscopic flexible structure with a metal layer. As a result, the flexible sensor will be stressed due to the bimetallic effect. Furthermore, a change in mass load can be detected as a change in the resonance frequency of the microscopic flexible structure. In order to detect biochemical reactions at the microscopic flexible structure surface, part of the microscopic flexible structure must be coated with a 'detector film' that reacts with the bio-molecules under investigation.

For experiments in liquid it has seen to be crucial to include reference measurements on a flexible structure which has not been coated with a detector film. If the coated and uncoated flexible structure are placed closely together in the same environment, the reference measurement can be used to cancel out background noise related to for example liquid movement and thermal drift.

By monitoring the stress formation in the microscopic flexible structure or the microscopic flexible structures resonance frequency as a function of time it is possible to study the kinetics of surface processes. One very promising application is to use an array of microscopic flexible structures in order to detect the presence of different kinds of molecules simultaneously.

Often, a change in mechanical properties is detected as a deflection of the microscopic flexible structure using an external optical system. However, for an array of microscopic flexible structures, this type of read-out becomes very complicated and operation in liquid is even more problematic. Moreover, this read-out depends on a measurable deflection of the microscopic flexible structure. For array and liquid applications it would therefore be advantageous to integrate a read-out mechanism on the microscopic flexible structure. Furthermore, an integrated piezoresisitve sensor would provide a direct measure of the stress formation in the microscopic flexible structure. At present, very few experiments have been carried out on biological systems, which normally implies a liquid environment, and microscopic flexible structures with integrated read-out have rarely been applied. Furthermore, the majority of the micro-cantilever-based experiments carried out until now have used micro-cantilevers developed for atomic force microscopy. Such micro-cantilevers are not necessarily optimally designed for biochemical sensing.

The microscopic flexible structure-based sensors have a huge potential, especially in the field of biochemical analysis. The detection technique can be used to construct smarter and simpler biochemical detectors, but it should also allow novel studies of single molecular interactions due to the extremely high mechanical sensitivity of micro-mechanical structures.

According to the present invention, the microscopic flexible structure-based biochemical sensor is fully integrated in a micro-channel suitable for liquid flow measurements and the device is preferably integrated with a micro-liquid handling system.

In a preferred embodiment of the present invention the sensor includes:

1) A supporting body, as shown in FIG. 1, made in silicon in which micro-channels are etched. The width of each channel is 100–500 $\mu$m and the depth is on the order to 100 $\mu$m. The length of the channel is on the order of mm.

2) Micro-cantilevers 2 which extend partially across the width of a micro-channel. The micro-cantilevers are attached to the sidewall of the channel. The micro-cantilevers are typically rectangular and are approximately 50 $\mu$m wide, 200 $\mu$m long and 1 $\mu$m thick. The micro-cantilevers are fabricated in silicon, silicon oxide and silicon nitride.

3) An integrated detection system 3 to measure changes in the mechanical properties of the micro-cantilever. This system preferably comprises piezoresistive elements on adjacent micro-cantilevers connected with similar resistive elements on the supporting body in order to form a Wheatstone bridge for accurate measurement of resistance changes in the piezoresistor. The piezoresistors are placed on top of the micro-cantilevers and the supporting body and they are fully encapsulated in dielectric layers such as silicon oxide and silicon nitride.

4) Electronic feed-throughs 4 which ensure electrical contact to the piezoresistive elements. The electrical wires are placed on top of the supporting body and the wire material is metal or highly doped silicon. The wires have a width of 100 $\mu$m, a thickness or approximately 1 $\mu$m and a length on the order of mm.

5) A spacer layer 5, which has to fully encapsulate the electrical wiring, so that liquid is not entering and short circuiting the electrical connections. The spacer layer has a thickness of 100 μm so that there is a clearance below and above the micro-cantilevers for the liquid to flow freely in the channel. The cover plate is fabricated in a UV curable polymer.

6) A cover plate 6 placed on top of the spacer layer. The cover plate has to form a hermetic sealing of the channel and is fabricated in a UV curable polymer and bonded to the spacer layer by a thermal treatment. The cover plate has a thickness of approximately 100 μm.

For specific applications the sensor might further comprise:

7) An integrated actuator mechanism 7, which can be used to drive the micro-cantilever at its resonance frequency or to induce a static bending of the micro-cantilever. The micro-cantilever is actuated by either electromagnetic/electrostatic forces or by integrating a piezoelectric layer or a heater element on the micro-cantilever. For electromagnetic/electrostatic actuation the micro-cantilever has to be coated with a conducting/magnetic material and externally exited by an electric/magnetic field.

8) A reference electrode 8 for electrochemical measurements. The electrode must be in contact with the liquid and can be inserted through the cover plate.

Other realisations can involve different materials. The spacer layer and cover plate can be fabricated in glass which is bonded to the silicon support body. Micro-cantilever and supporting body can be fabricated in polymer materials and the channels can be formed by embossing or injection moulding.

Other realisations can involve different detection techniques, such as external optical detection through the cover plate or integrated optical systems where a displacement of the micro-cantilever modifies the transmission of an optical waveguide placed on or near the micro-cantilever. Other integrated detection principles could be piezoelectric or capacitive. For piezoelectric detection of the micro-cantilever deflection a piezoelectric film is placed on the micro-cantilever, and for capacitive measurements the micro-cantilever is coated by a conducting film and a counter electrode is placed below or above the micro-cantilever.

Figure 2:
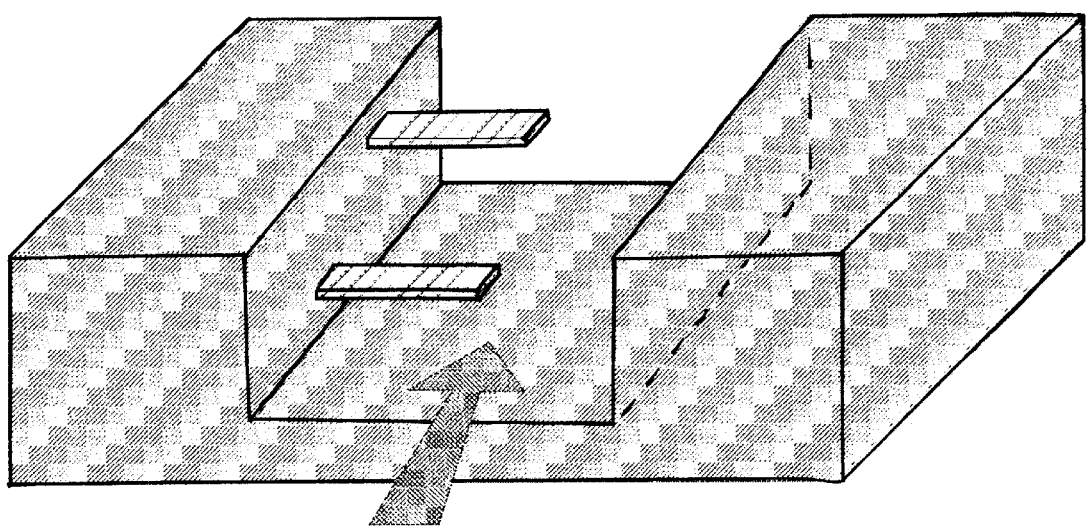
FIG. 2: Recessed micro-cantilevers placed in a micro-channel.

Other realisations can involve recessed micro-cantilevers (FIG. 2), so that there is no need to form a spacer layer, or so that the cover plate can be eliminated, relying instead on capillary flow to guide fluids through channels. Furthermore, recessed micro-cantilevers can be used to perform measurements at different heights in the liquid. Moreover, the micro-cantilevers can be placed perpendicular to the liquid flow and micro-cantilevers can be placed on either side of the channel.

Figure 3:
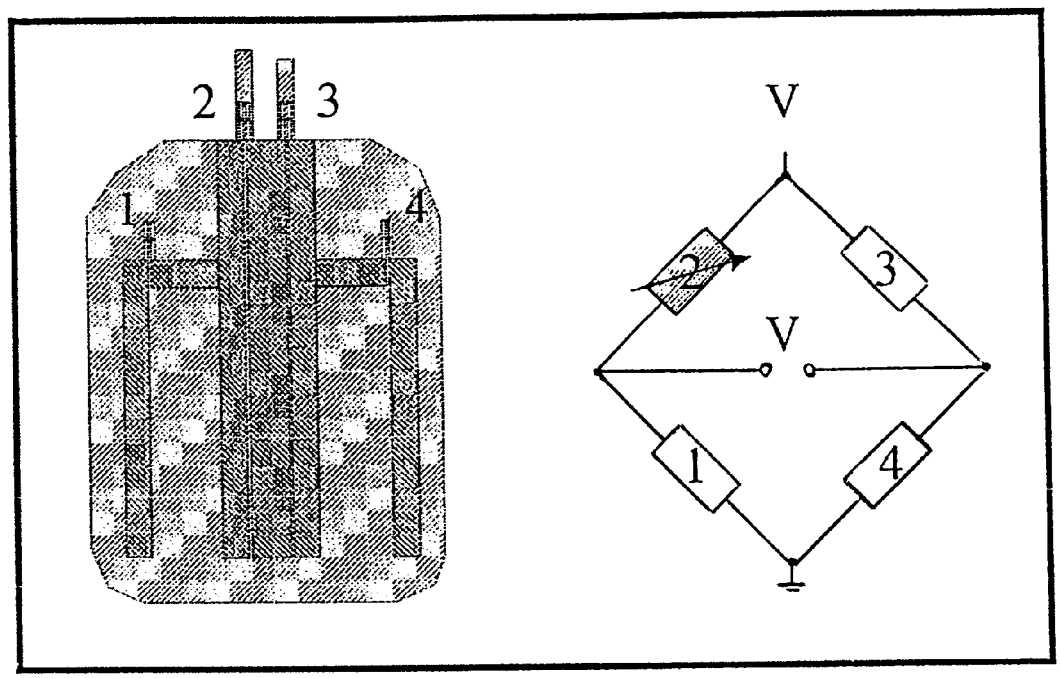
FIG. 3: Two micro-cantilever resistors and two support resistors placed in a Wheat-stone bridge.

On each micro-cantilever one piezoresistive element is placed. By connecting two micro-cantilevers and two resistors on the supporting body in a Wheatstone bridge (FIG. 3) it is possible to perform a common mode rejection of noise in the system. One micro-cantilever then serves as a reference micro-cantilever whereas the other is used to detect a specific biochemical reaction. A reference measurement is crucial in liquid where turbulence and thermal drift have a significant influence on the measurement.

Figure 4:
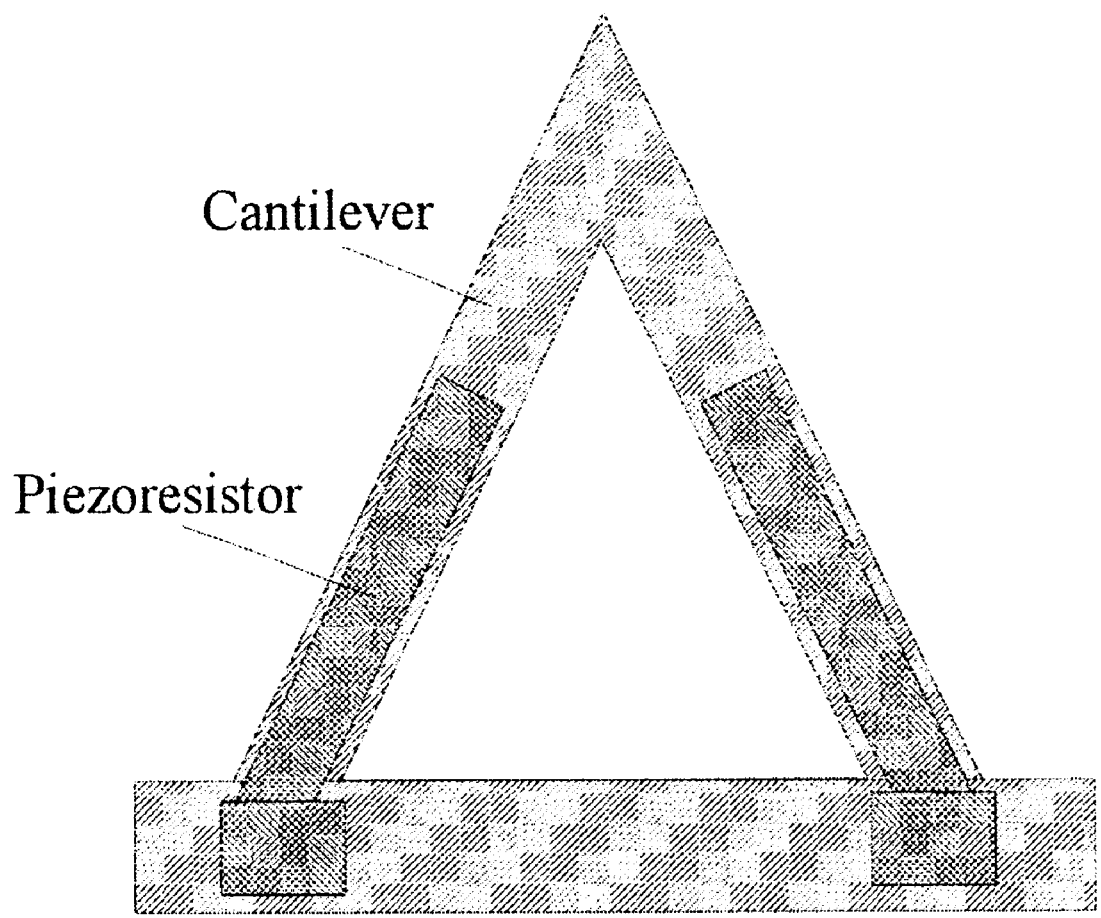
FIG. 4: Schematic drawing of triangular micro-cantilever with one piezoresistor placed on each arm.

Other realisations can involve triangular shaped micro-cantilevers with piezoresistors placed on each of the two arms forming the triangular micro-cantilever (FIG. 4). This will enable the torsion as well as the vertical deflection of the micro-cantilever to be detected.

Other realisations can involve micro-bridges and micro-membranes instead of micro-cantilevers.

In a second embodiment of the present invention, a complete micro-cantilever, micro-bridge or micro-membrane transducer system comprises the microstructure described in the above preferred embodiment of the invention, as well as:

1) External electrical connections to the micro-cantilever, micro-bridge or micro-membrane system, to apply a controlled voltage to the piezoresistive elements placed in Wheatstone bridges and to monitor the electrical output from the piezoresistors.

2) Voltage sources amplifiers and voltmeters to detect changes in the piezoresistors due to a micro-cantilever bending.

3) AC voltage source to apply AC signals to the piezoresistors for actuation or resonance detection.

4) External fluidic connection to the micro-channels to pump fluids in and out of the micro-channels.

Fabrication

The said sensor fully integrated in a micro-channel is fabricated by use of micro-machining. This technique allows dimensions in the micrometer regime and high reproducibility. For the fabrication of a micro-bridge or a micro-cantilever sensor the fabrication is exactly the same and only the design differs. In the following examples the resistors are defined in poly-crystalline silicon. By using a silicon-on-insulator wafer the resistors can be defined in single-crystalline silicon which exhibits higher signal-to noise ratio.

EXAMPLE 1

Micro-cantilever-based Sensor

In the following, the fabrication of a micro-cantilever-based sensor is described. The micro-cantilever consists of 5 layers, where one of the layers serves as the piezoresistor. The sensor could also be formed with only three layers: A layer defining the piezoresistor and a layer on both sides of the resistor for the encapsulation.

The starting material is a 500 μm thick single side polished <100> silicon wafer. A 100–1000 nm thick thermal oxide is grown in order to form an etch-stop layer for the later micro-cantilever releasing and channel etch process. FIGS. 5.*a*–5.*l* show, in a side view, a schematic illustration of the process. A low pressure chemical vapour deposition (LPCVD) poly-silicon layer, 300–800 nm thick, is deposited on top of the oxide, succeeded by the growth of 500–1000 nm thick oxide for the fabrication of stress compensated micro-cantilevers (FIG. 5.*b–c*).

A 200–350 nm LPCVD poly-silicon layer is deposited on top of the oxide. This layer defines the piezoresistive elements (piezoresistors) (FIG. 5.*d*). Boron is implanted in the poly-silicon to obtain approximately a doping concentration of about $3.10^{19}$ cm$^{-3}$. At this doping level a high gauge factor (K=30) and a low TCR (temperature coefficient of resistance) value (FIG. 5.*e*) are obtained.

A photo resist layer is spun on top of the wafer, and the resistor pattern is transferred to the resist by photolithography. The resistors are then anisotropically etched in the poly-silicon by reactive ion etching (RIE) in order to obtain well-defined resistor dimensions (FIG. 5.*f*).

Micro-cantilever and channel are then defined by a second photolithography step. The oxide/silicon/oxide layer can then be etched by either (FIG. 5.*g*):

a)
   1. Hydrofluoric acid (HF) etching of the top oxide layer
   2. Anisotropic RIE of the silicon
   3. HF etching of the bottom oxide layer or b)
1. Anisotropic RIE of the oxide
2. Anisotropic RIE of the silicon
3. Anisotropic RIE of the oxide In order to encapsulate the resistors and to protect the micro-cantilever sidewalls when KOH/RIE etching of the channel, a 50–200 nm thick thermal oxide is grown on top of the resistor (FIG. 5.h). Hereafter, a 20–100 nm thick LPCVD nitride is deposited to be used as an etch mask, but also as a diffusion barrier (FIG. 5.i).

For the fabrication of contact holes through the nitride/oxide layer, a thin resist is spun on top of the wafer. The contact-hole mask is transferred to the resist by photolithography. The nitride is etched by RIE and the oxide is etched by HF. The nitride/oxide in the channels are also removed (FIG. 5.j).

Metal for electrical connections, typically chromium/gold or aluminium are deposited by lift-off technique. This is done by spinning a thin layer of resist on top of the wafer. The metal wire mask is transferred to the resist by photolithography. The metal is evaporated on top of the wafer and finally the resist is stripped in acetone leaving the metal wires on top of the support structure(FIG. 5.k).

For the use of metal as an immobilisation layer on the micro-cantilever, a metal layer is deposited on top of the micro-cantilever also by lift-off (FIG. 5.l). By depositing micro-cantilever metal in a second lift-off step, it is possible to use other metals and metal thicknesses than used for the electrical connections. Another metal layer can be deposited on the reference micro-cantilever in order to make the two micro-cantilevers as identical as possible.

Figure 6:
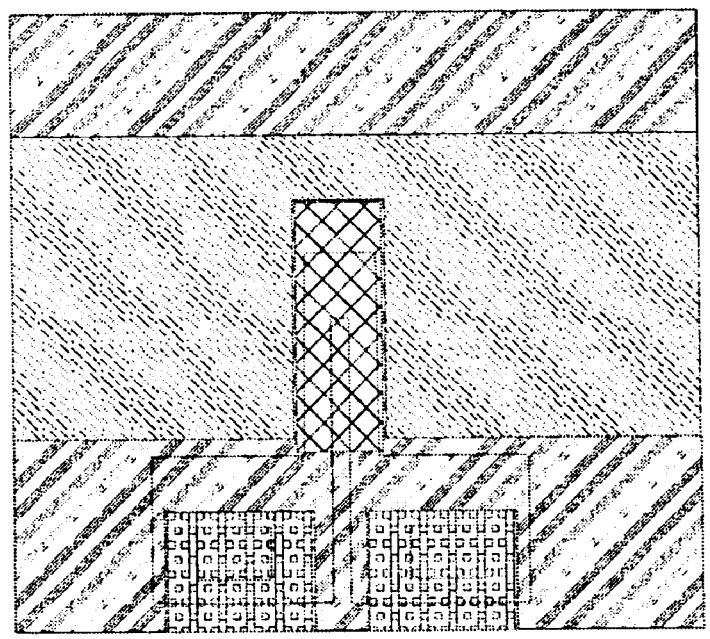
FIG. 6: Schematic top view of the micro-cantilever-based biochemical sensor after the fabrication of the lower part of the channel

A schematic top view of the micro-cantilever-based biochemical sensor at this point in the fabrication is shown in FIG. 6. The top of the channel structure is coated by nitride and the sides and the bottom of the etched channel is silicon. The micro-cantilever is coated by an optional metal layer for immobilisation of molecules, and the micro-cantilever has a piezoresistor-integrated. The piezoresistor has two contact pads to which metal wires have been connected.

In order to integrate the sensor in a closed channel, a top part of the channel is required. The upper part of the channel can be fabricated by two different principles:

1. The channel can be fabricated by depositing a spacer layer in polymer, which actually defines the sidewalls of the top part of the channel. A cover lid is then bonded or glued to the polymer.
2. The upper part of the channel is etched in a glass or silicon wafer, which is bonded or glued to the micro-cantilever wafer.

The two fabrication procedures are described below:
Principle number 1 can be split out in two fabrication procedures:

1a) Closed Reactive Ion Etched Channel with Polymer Spacer

A 30–100 μm thick photosensitive polymer layer is spun on the top side of the wafer seen in FIG. 5.m. The spacer mask is transferred to the photosensitive polymer by photolithography, see FIG. 7.a.

It is now possible to etch the channel and release the micro-cantilever by isotropic RIE using the metal on the micro-cantilever and the photosensitive polymer as etch masks. The depth of the channel is between 30–100 μm (FIG. 7.b).

Figure 7:
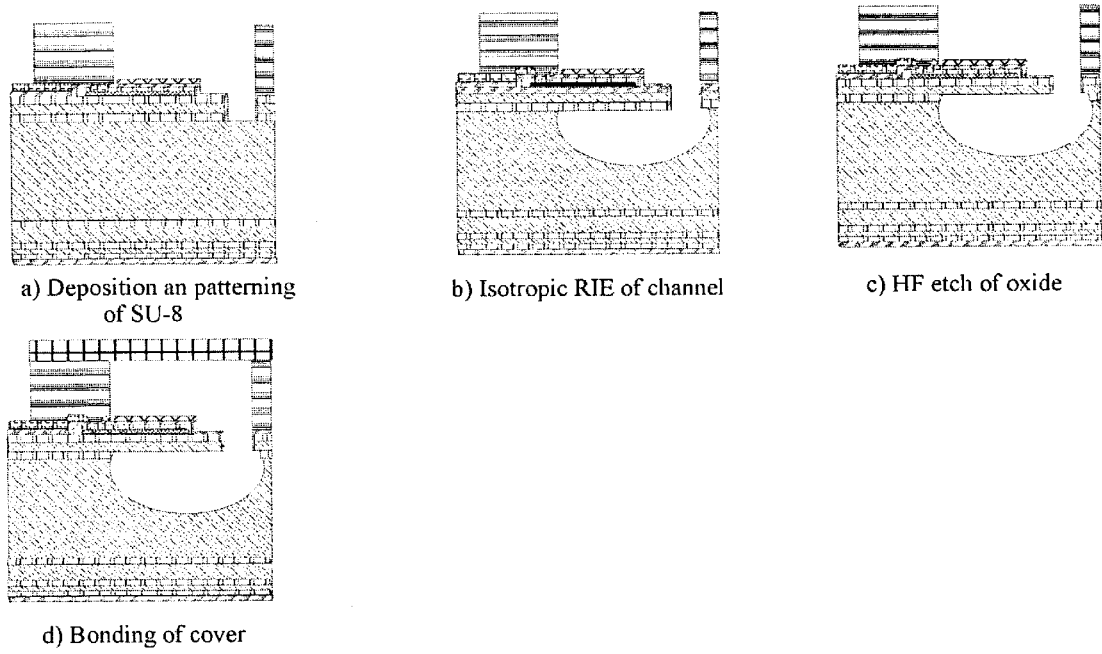
FIG. 7: Schematic cross-sectional view of the process sequence, with the lower part of the channel defined by RIE and the upper part of the channel defined by the use of a photosensitive polymer as spacer layer FIG. 8 Schematic cross-sectional view of the process sequence, with the lower part of the channel defined by wet etching and the upper part of the channel by use of a photosensitive polymer as spacer layer

The oxide below the micro-cantilever is etched by HF, yielding a stress compensated micro-cantilever (FIG. 7.c).

Finally, a top plate consisting of silicon, Pyrex, polymer or any combination of these is sealed to the photosensitive polymer walls either by gluing or by local heating of the top of the photosensitive polymer layer. The melted polymer will form a bond to the top plate (FIG. 7.d).

1b) Closed KOH Etched Channel with Polymer Spacer

In order to fabricate a well-controlled channel the wafer is etched in KOH after the micro-cantilever has been defined and the micro-cantilever metal has been deposited. The metal and the nitride on the micro-cantilever act as etch masks in this process. The KOH etch is finished when the micro-cantilever is released resulting in a channel depth of 30–100 μm, see FIG. 8.a.

Figure 8:
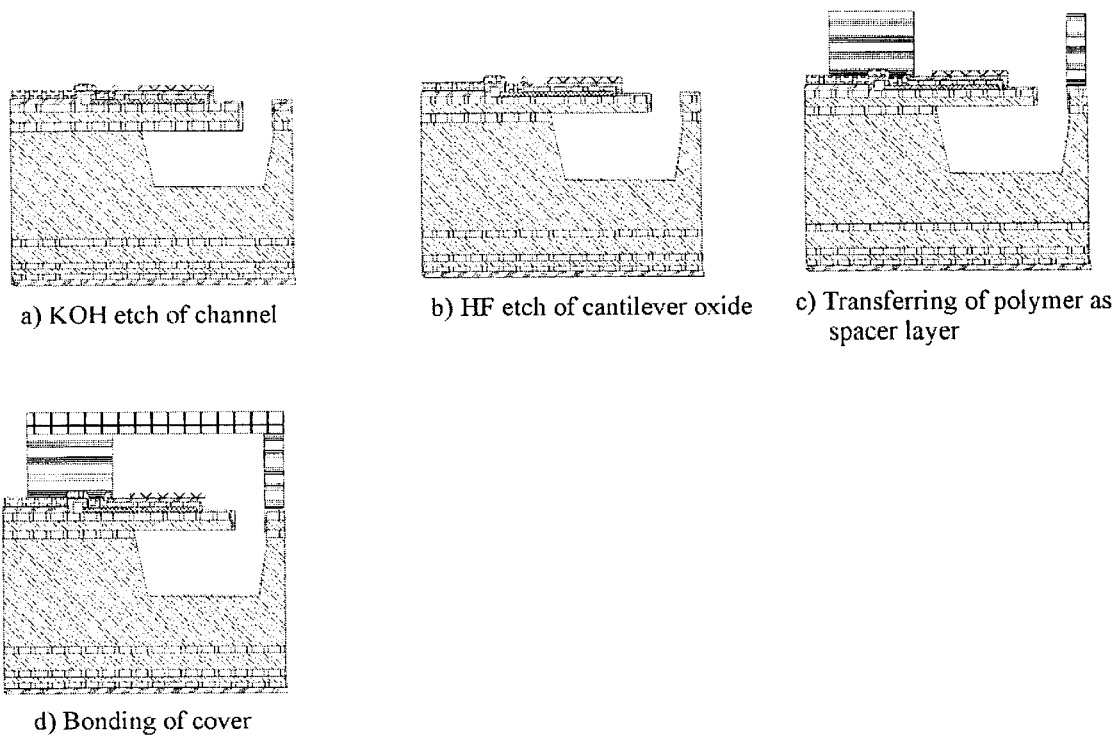

The oxide below the micro-cantilever is etched by HF, yielding a stress compensated micro-cantilever (FIG. 8.b).

A 30–100 μm thick polymer layer is transferred to the top side of the wafer, defineing the spacer layer see FIG. 8.c.

Finally, a top plate consisting of silicon, Pyrex, polymer or any combination of these is sealed to the photosensitive polymer walls either by gluing or by local heating of the top of the photosensitive polymer layer. The melted polymer will form a bond to the top plate (FIG. 8.d).

2): Closed Channel by Bonding the Top and the Bottom Part of the Channel

In order to fabricate a well-controlled channel the wafer is etched in KOH after the micro-cantilever metal has been deposited. The metal and the nitride act as etch masks in this process. The KOH etch is finished when the micro-cantilever is released resulting in a channel depth of 30–100 μm, see FIG. 9.a.

The oxide below the micro-cantilever is etched in HF, yielding a stress compensated micro-cantilever (FIG. 9.b).

A 20–200 nm thick LPCVD nitride layer is deposited on a 500 μm thick single side polished <100> silicon wafer in which the top part of the channel is to be defined (FIG. 9.c).

Thin resist is spun on the back side of the wafer, and a mask defining the holes for contacting the metal wires is transferred by photolithography. The pattern is transferred to the nitride by RIE (FIG. 9.d). The exposed silicon areas are then etched in KOH. The KOH etch is stopped when the created micro-membranes have a thickness 30–100 μm (FIG. 9.e).

Thin resist is then spun on the front side of the wafer and a mask defining the channel and holes for contacting the metal wires is transferred to the resist by photolithography. The pattern is transferred to the nitride by RIE (FIG. 9.f). The channel and the contact-hole are then etched until the 30–100 μm micro-membrane is etched away at the contact hole, resulting in a channel depth of 30–100 μm (FIG. 9.g).

Between 2–10 μm glass is evaporated on the front side of the wafer for the anodic bonding process (FIG. 9.h). Finally, the two wafers are bonded by anodic bonding (FIG. 8.i).

Instead of using KOH etch in order to fabricate the upper part of the channel and the contact holes, it is possible to use RIE instead. It is also possible to use a Pyrex wafer instead of a silicon wafer. For a Pyrex wafer HF is used to isotropically etch the channel and the contact-holes.

EXAMPLE 2

Micro-membrane-based Sensor

For the fabrication of a micro-membrane-based sensor in a channel, the fabrication is also performed by micromachining. In contrast to the micro-cantilever or micro-bridge-based sensor, the micro-membrane is normally placed in the bottom of the channel. This design makes it possible to contact the resistors from the backside. Nevertheless, in following example the resistors will be contacted from the same side as the channel.

The first steps (FIG. 5.a.–5.f.) in the fabrication sequence is basically the same as descriebed for the micro-cantilever or micro-bridge based sensor.

After the resistors have been defined by RIE the resistors are encapsulated in a 50–200 nm thick thermal oxide. Hereafter, a 20–100 nm thick LPCVD nitride is deposited to be used as an etch mask, but also as a diffusion barrier (FIG. 10.a.).

For the fabrication of contact holes through the nitride/oxide layer, a thin resist is spun on top of the wafer. The contact-hole mask is transferred to the resist by photolithography. The nitride is etched by RIE and the oxide is etched by HF (FIG. 10.b.).

Metal for electrical connections, typically chromium/gold or aluminium are deposited by lift-off technique. This is done by spinning a thin layer of resist on top of the wafer. The metal wire mask is transferred to the resist by photolithography. The metal is evaporated on top of the wafer and finally the resist is stripped in acetone leaving the metal wires on top of the support structure (FIG. 10.c.).

Figure 10:
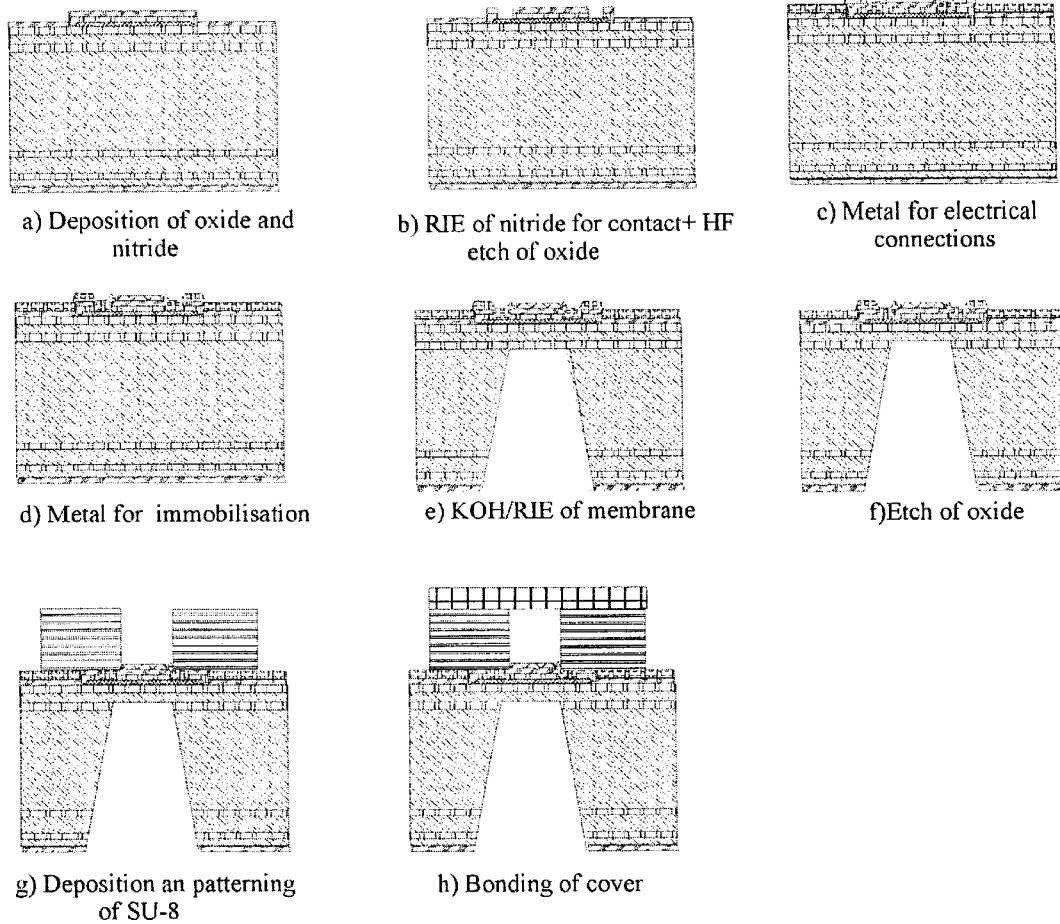
FIG. 10: Schematic top view of the micro-membrane-based biochemical sensor with the channel made of a photosensitive polymer.

For the use of metal as an immobilisation layer on the micro-cantilever, a metal layer is deposited on top of the micro-membrane also by lift-off (FIG. 10.d.). By depositing micro-cantilever metal in a second lift-off step, it is possible to use other metals and metal thicknesses than used for the electrical connections.

The micro-membrane is now defined by KOH etching from the backside. First, a thin resist layer is spun on the backside of the wafer. The backside mask is the tranferred to the resist. Hereafter, the nitride/silicon/oxide sandwich is etched in RIE. The wafer is then etched in KOH, where the oxide will act as a etchstop. (FIG. 10.e.).

The oxide is then removed in a HF etch (FIG. 10.f.).

A channel is now fabricated on top of the micro-membrane. This can be fabricated by two different principles:

1. The channel can be fabricated by depositing a spacer layer in polymer, which actually defines the sidewalls of the top part of the channel. A cover lid is then bonded or glued to the polymer.
2. The upper part of the channel is etched in a glass or silicon wafer, which is bonded or glued to the micro-cantilever wafer.

The two fabrication procedures are described below:
1) Spacer Layer in Polymer

A 30–100 µm thick photosensitive polymer layer is spun on the top side of the wafer. The spacer mask is transferred to the photosensitive polymer by photolithography, see FIG. 10.g.

Finally, a top plate consisting of silicon, Pyrex, polymer or any combination of these is sealed to the photosensitive polymer walls either by gluing or by local heating of the top of the photosensitive polymer layer. The melted polymer will form a bond to the top plate (FIG. 10.h).

2) Closed Channel by Bonding the Top Part to the Substrate

This method is exactly the same as described in the "Closed channel by bonding the top and the bottom part of the channel" section in the fabrication sequence of a micro-cantilever-based sensor in a channel.

APPLICATIONS OF THE PRESENT INVENTION

In the following, examples of different applications of the present invention are listed and commented. The application of the present invention should however not be limited to the listed examples.

Laminated Flow

Figure 11:
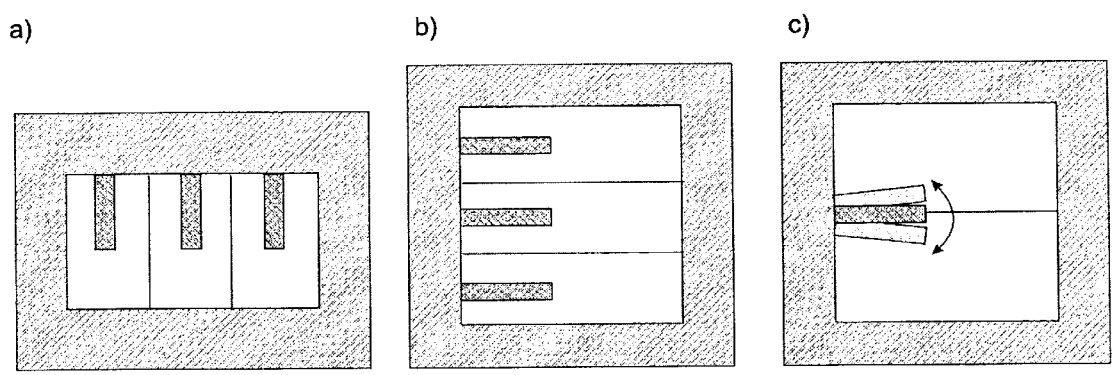
FIG. 11: Principle of exposing closely spaced micro-cantilevers to different chemical environments by using vertically laminated flow (a), horizontally laminated flow (b) and by moving the micro-cantilever through different layers of laminated flow (c).

Adjacent or very closely spaced micro-cantilevers can be exposed to different chemical environments at the same time by (FIG. 11).

1) Laminating the fluid flow vertically in the micro-channel into two or more streams, so that micro-cantilevers on opposing sides of the micro-channel are immersed in different fluids.
2) Laminating the fluid flow horizontally in the micro-channel, so that micro-cantilevers recessed to different levels in the micro-channel are immersed in different fluids.
3) Laminating the fluid flow either horizontally or vertically and moving the micro-cantilevers through the different fluids by actuating the micro-cantilevers.

In this way, micro-cantilever signals from different fluid environments can be compared. Moreover the technology can be used for coating narrowly spaced micro-cantilevers with different chemical substances. Examples on both aspects will be described below.

Functionalisation

Functionalising the micro-cantilevers can be performed using conventional immobilisation chemistry, which easily applies to the micro-cantilever materials. However, for the closely spaced micro-cantilevers in micro-channels new technologies for applying the different coatings are needed. The functionalisation of narrowly spaced micro-cantilevers can be performed by one or more of the technologies described below:

1) In the micro-fabrication of the device, the micro-cantilevers can be coated with different thin film layers which are compatible with the fabrication process. The thin films can be metal, silicon and dielectric layers. The different thin films can then be used to bind molecules which have a specific binding to a specific thin film.
2) The molecules to be attached on the micro-cantilever surface can be synthesised with a photo activated binding site. Molecules are then attached to the micro-cantilever surface by placing the micro-cantilever in a liquid solution with the coating molecules and exposing the micro-cantilever to UV light. The UV light induces the creation of a bond between the micro-cantilever surface and molecules. This coating can be performed in the channel after it has been closed, by injecting different coating molecules in the channel and illuminating the micro-cantilevers individually through the cover plate. By scanning a laser across the device small well-defined areas can be coated with specific coatings. Between each coating the system must be rinsed and a new coating solution injected in the channels.
3) Using an inkjet printer principle small droplets of liquid can be delivered. These systems are commercially available for DNA chip fabrication. Such a liquid delivery system can be used to spray droplets of different liquids on closely spaced micro-cantilevers. The delivered droplets typically have a diameter of 100 µm. This coating technique must be performed before the channel is sealed.
4) When the channels are sealed, laminated flow can be used to coat narrowly spaced micro-cantilevers by having two or more laminated flows in the system. Micro-cantilevers placed in different heights and/or on different sides of the channel will thus be immersed in different liquids. After coating, the micro-channels can be flushed with other fluids to remove the residual coating material. By repeating the technique, several layers of coating can be added to the micro-cantilever. In order to bind molecules to only one side of the micro-cantilever photoimmobilisation or pre-deposited thin films can be used.

5) Selective coating can be performed by laminating two or more streams in the micro-channel and placing the micro-cantilever in one of the streams by a static bending. Moreover, a controlled movement of the micro-cantilever through separated laminated streams can be used to coat the micro-cantilever with multiple layers such as glutaraldehyde-avidin-biotin.

6) Selective and reversible coating of the micro-cantilever, with for example metalloproteins, can be acheived electrochemically. A conducting layer on the micro-cantilever can be used as the working electrode. The counter electrode might be an integrated part of the system. Also it is often desirable to include a reference electrode for control of the applied potential.

Reference Micro-cantilever and Reference Measurement

Figure 12:
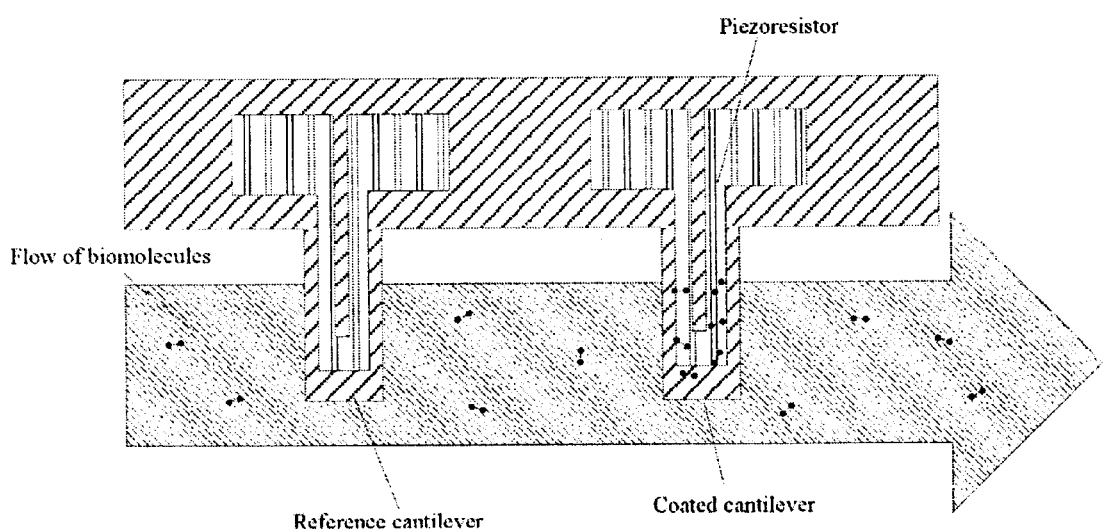
FIG. 12: Principle of using one micro-cantilever as measurement micro-cantilever and the other micro-cantilever as reference.

To minimise the effect of turbulence and thermal drift in the system, a reference micro-cantilever can be implemented. The reference micro-cantilever is placed close to the measurement micro-cantilever and in the same measurement environment. However, the reference micro-cantilever is not coated with a detector film. The reference micro-cantilever might be coated with another film which does not act as a detector or which detects a second substance. By subtracting the reference signal from the measurement signal most background noise can be eliminated, see FIG. 12.

Figure 13:
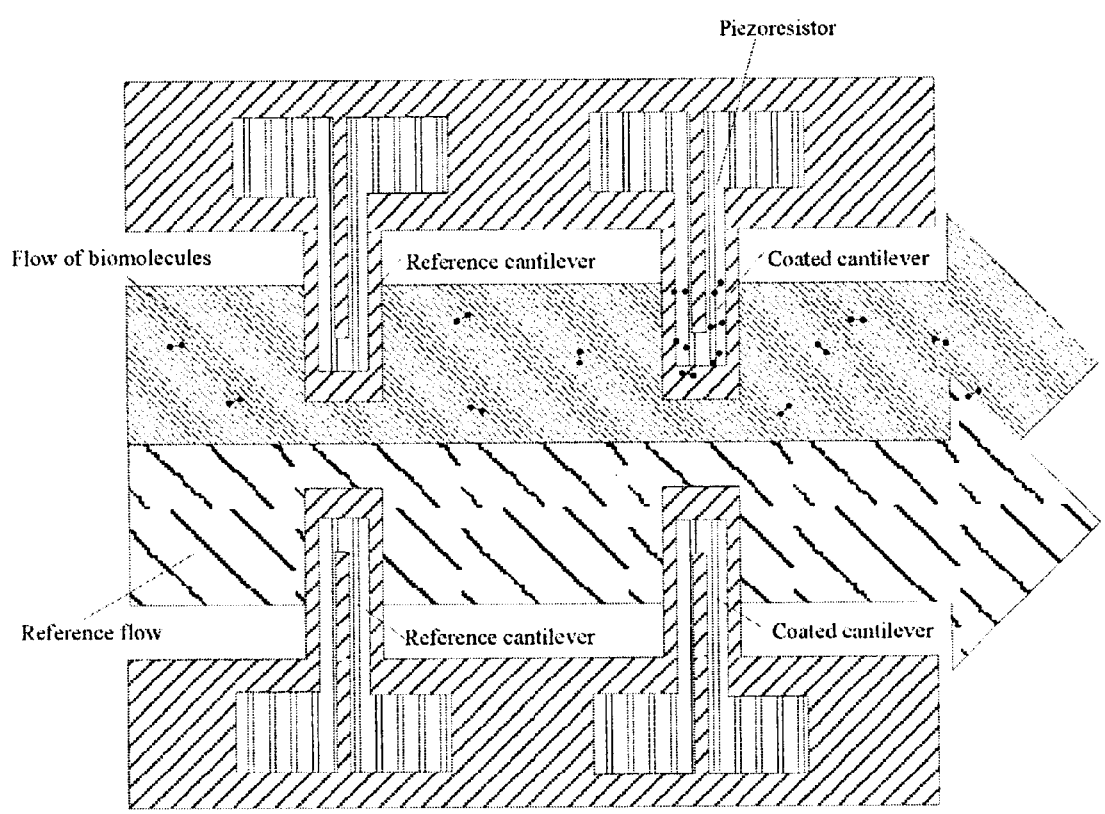
FIG. 13: Principle of using two laminar flow. One as the measurement flow and the other as a reference flow.

For most biochemical applications it is important to perform a reference measurement in a reference liquid. Often it is the increase/decrease in the concentration of a specific molecule which is of interest. For such relative measurements a reference liquid is necessary. The micro-cantilever placed in the reference solution should be identical to the measurement micro-cantilever in the measurement solution, see FIG. 13. The measurement solution and the reference solution can be investigated in the same channel at the same time by laminating the flow and let the two streams run in parallel. Micro-cantilevers placed on either side of the channel will measure the reaction in two different fluids. Quasi-simultaneous measurements in analytes and in reference solutions can be performed by moving the micro-cantilever through the two liquids.

Diffusion Measurements in Added Layers

Molecules entering the detector films on the micro-cantilever change the stress of the film, which results in a micro-cantilever bending. For example, diffusion in cell micro-membranes can be investigated and the activity of specific micro-membrane channels which are regulated by voltage or by the binding of another molecule can be investigated.

Figure 14:
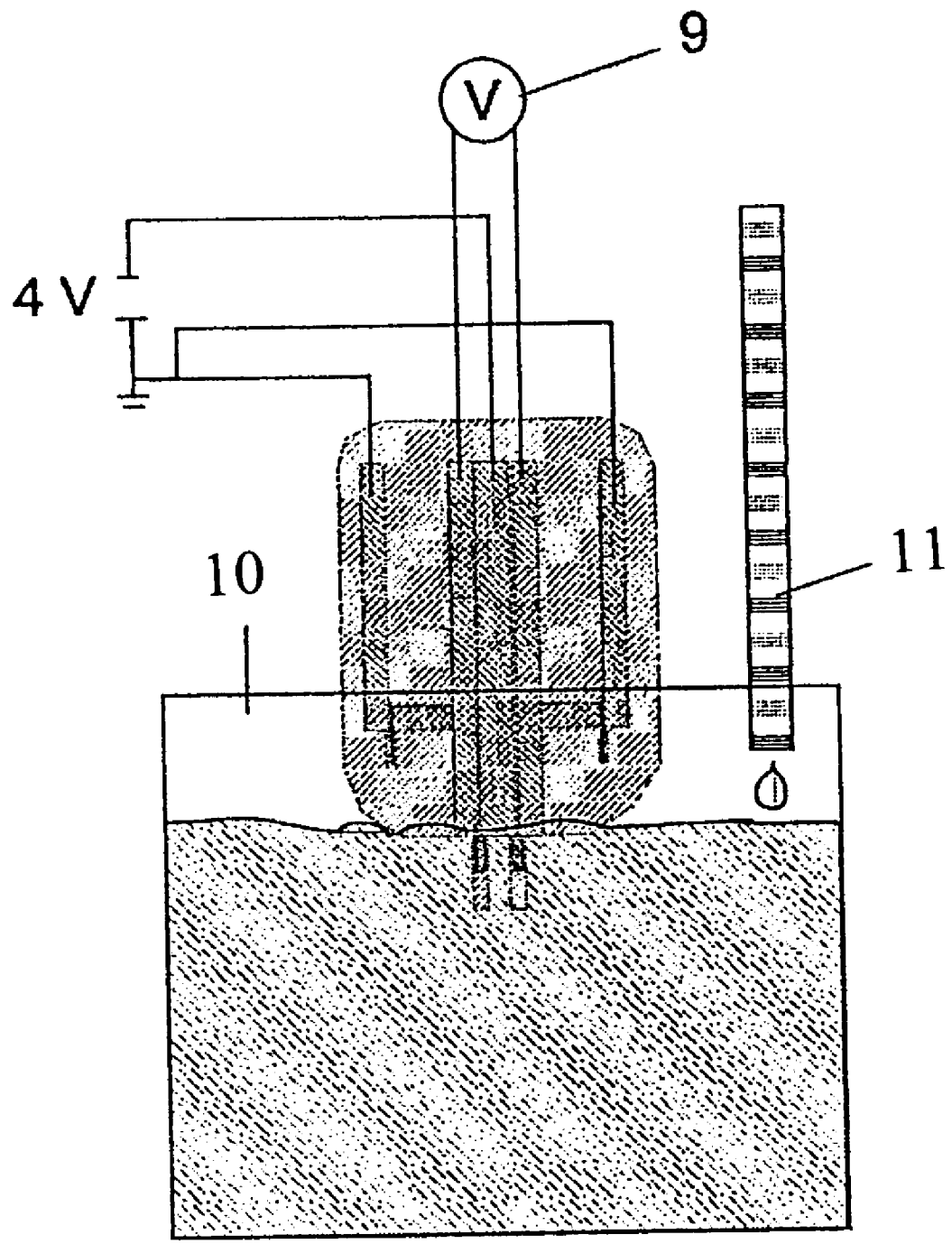
FIG. 14: Experimental set-up for the measurement of alcohol diffusion in a polymer coated micro-cantilever.

Preliminary experiments on the diffusion of alcohol in polymers have been performed using micro-cantilevers with piezoresistive read-out. One of two micro-cantilevers integrated in a Wheatstone bridge is coated with a UV sensitive resist in which the stress is changed when subjected to alcohol. FIG. 14 shows micro-cantilevers placed in a small open liquid container 7 with DI water. Liquid alcohol is injected 8 and the output voltage from the Wheatstone bridge is recorded 9 as a function of time. The output voltage from the Wheatstone bridge reflects the difference in the deflection of the two micro-cantilevers.

Figure 15:
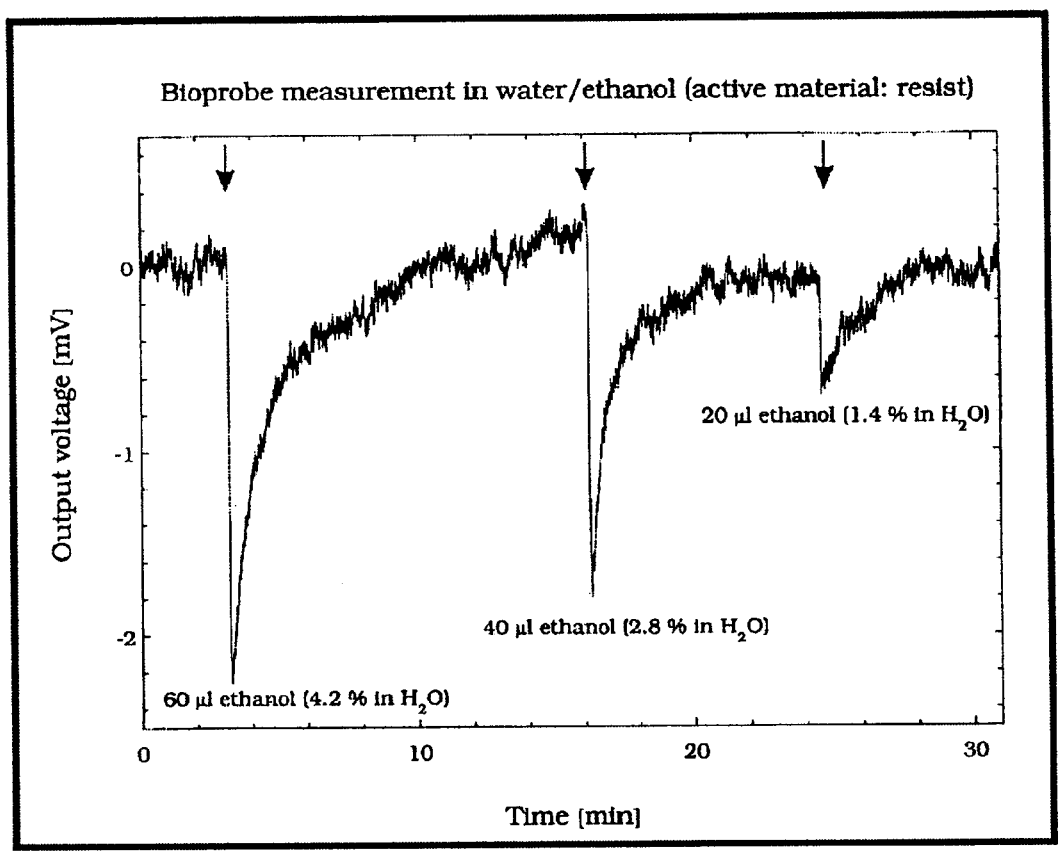
FIG. 15: Micro-cantilever response to injected alcohol as a function of time.

The micro-cantilever response to three different amounts of Ethanol is shown in FIG. 15. The arrows indicate the times at which new alcohol is placed on the surface of the water, close to the micro-cantilever. It is clearly seen, how the micro-cantilever responds immediately to the alcohol after which the signal decreases as the alcohol is diluted in the water and evaporated from the surface. The magnitude of the signal reflects the amount of injected alcohol. Thus the diffusion of alcohol into the polymer causes the stress in the polymer to change. The process is reversible and when the alcohol leaves the film, the micro-cantilever returns to the start position. The mechanism can be used to construct a sensor for measuring alcohol concentrations in liquid.

The time dependent micro-cantilever response can also be used to investigate the dynamics of layer formation on the micro-cantilever surface. For example the formation of self-assembled monolayers can be investigated.

Conformal Changes of Protein Layers

Conformal changes of proteins adsorbed on a micro-cantilever will give rise to a change in resonance frequency and stress of the micro-cantilever. Hereby it is possible to study the conformal changes of proteins caused by external parameters such as pH-value, ion-concentration and temperature. For example the metalloprotein azurin adsorbed on gold is know to undergo conformational changes when subjected to different pH-values. How azurin binds to gold, and how the binding is changed when the pH-value is changed is not well understood, and the micro-cantilever-based measurements can give additional information on the binding properties. Many active enzyme functions also results in stress changes. Thereby enzyme activity levels in different environments can be investigated.

Gene Detection

One of the major applications of the invention is the detection of multiple disease-associated genes. Single stranded DNA from the disease-associated genes is attached to micro-cantilevers by one of the coating technologies described above using conventional binding chemistry. Narrowly spaced micro-cantilevers placed in one channel can be coated with DNA sequences from different genes. A treated blood sample consisting of single stranded DNA is then flushed through the system. If one of the disease-associated genes is present in the sample it will bind specifically to the corresponding DNA string attached to the micro-cantilever. DNA strings, which have been non-specifically bounded can be detached by a heat treatment. The specific binding will result in a surface stress change as well as in a resonance change of the micro-cantilever. Hereby it is possible to perform a screening of several genes simultaneously. The method could also apply to DNA sequencing.

Antigen-antibody Reaction

The idea of screening for specific genes can be expanded to the detection of different antibodies. For this application closely spaced micro-cantilevers are coated with different antigens, using conventional binding chemistries. Antibodies bind specifically to antigens, whereby it is possible to screen for different antibodies in a blood sample.

Electrochemistry

Applying a conducting layer on the micro-cantilever and a reference electrode in the channel it is possible to perform electrodeposition and electrochemistry on layers on a micro-cantilever surface. For example in can be investigated how the stress in layers of mettaloproteins such as azurin and yeast cytochrom c respond to different potentials. Furthermore redox-processes might be monitored. Moreover, the adsorption and desorption of electrodepositable molecules can be investigated.

What is claimed is:

1. A sensor for detecting the presence of a substance in a liquid, said sensor comprising:

means for handling the liquid, said handling means comprising an interaction chamber of micrometer dimensions, an inlet and an outlet, a first flexible member having a surface, said surface holding a substance, wherein the surface holding the substance is at least partly positioned inside the interaction chamber so that at least part of the substance is exposed to the liquid, and means for detecting a mechanical parameter associated with the first flexible member, said mechanical parameter being related to the presence of the substance in the liquid;

wherein the interaction chamber, inlet and outlet of said means for handling are arranged to establish laminar flow across said first flexible member.

2. A sensor according to claim 1, wherein the first flexible member comprises a cantilever having a first and a second end, wherein the first end is attached to the interaction chamber.

3. A sensor according to claim 1, wherein the first flexible member comprises a bridge having a first and a second end, wherein the first and second ends are attached to the interaction chamber.

4. A sensor according to claim 1, wherein the first flexible member forms part of a boundary defining the interaction chamber.

5. A sensor according to claim 1, wherein the detecting means for detecting the mechanical parameter associated with the first flexible member comprises a piezoresistive element, said piezoresistive element being an integral part of the first flexible member.

6. A sensor according to claim 1, wherein the detecting means for detecting the mechanical parameter associated with the first flexible member comprises a laser, an optical element and a position sensitive photo detector.

7. A sensor according to claim 5, wherein the piezoresistive element forms part of a balanced bridge, such as a Wheatstone bridge.

8. A sensor according to claim 1 further comprising an actuator for moving the flexible member relative to the interaction chamber.

9. A sensor according to claim 8, wherein the actuator comprises a piezoelectric element.

10. A sensor according to claim 8, wherein the actuator comprises means for providing an electrostatic induced movement of the flexible member.

11. A sensor according to claim 8, wherein the actuator comprises means for providing a magnetic induced movement of the flexible member.

12. A sensor according to claim 8, wherein the actuator comprises means for providing a thermal induced movement of the flexible member.

13. A sensor according to claim 1, wherein the handling means is fabricated in a material selected from the group consisting of metals, glasses, polymers or semiconductor materials, such as silicon.

14. A sensor according to claim 1, wherein the substance being held by the surface of the first flexible member is selected from the group consisting of metals, polymers, biochemical molecules or micro-biochemical structures.

15. A sensor according to claim 1, further comprising
a second flexible member being at least partly positioned inside the interaction chamber so that at least part of the second flexible member is exposed to the fluid, and
means for detecting a mechanical parameter associated with the second flexible member.

16. A sensor according to claim 15, wherein the detecting means comprises a piezoresistive element, said piezoresistive element being an integral part of the second flexible member, and wherein the piezoresistive element forms part of a balanced bridge, such as a Wheatstone bridge.

17. The sensor of claim 1 wherein said interaction chamber is between 50 and 500 $\mu M$ in at least one of width or depth dimensions.

18. The sensor of claim 1 wherein said means for detecting detects a stress change in said first flexible member.

19. The sensor of claim 1 wherein said mechanical parameter sensed by said means for detecting is a static parameter related to stress in said flexible member.

20. A sensor for detecting the presence of a substance in a liquid, said sensor comprising:
means for handling the liquid, said handling means comprising an interaction chamber of micrometer dimensions, an inlet and an outlet,
a first flexible member having a surface, said surface holding a substance, wherein the surface holding the substance is at least partly positioned inside the interaction chamber so that at least part of the substance is exposed to the liquid, and
means for detecting a mechanical parameter associated with the first flexible member, said mechanical parameter being related to the presence of the substance in the liquid, wherein the detecting means form an integral part of the first flexible member;
wherein the interaction chamber, inlet and outlet of said means for handling are arranged to establish laminar flow across said first flexible member.

21. A sensor according to claim 20, wherein the first flexible member comprises a cantilever having a first and a second end, wherein the first end is attached to the interaction chamber.

22. A sensor according to claim 20, wherein the detecting means for detecting the mechanical parameter associated with the first flexible member comprises a piezoresistive element.

23. A sensor according to claim 22, wherein the piezoresistive element forms part of a balanced bridge, such as a Wheatstone bridge.

24. A sensor according to claim 21 further comprising an actuator for moving the second end of the cantilever relative to the interaction chamber.

25. A sensor according to claim 24, wherein the actuator comprises a piezoelectric element, said piezoelectric element being an integral part of the cantilever.

26. A sensor according to claim 20, wherein the handling means is fabricated in a material selected from the group consisting of metals, glasses, polymers or semiconductor materials, such as silicon.

27. A sensor according to claim 20, wherein the substance being held by the surface of the first flexible member is selected from the group consisting of metals, polymers, biochemical molecules or micro-biochemical structures.

28. A sensor according to claim 20, further comprising
a second flexible member being at least partly positioned inside the interaction chamber so that at least part of the second flexible member is exposed to the fluid, and
means for detecting a mechanical parameter associated with the second flexible member.

29. A sensor according to claim 28, wherein the detecting means comprises a piezoresistive element, said piezoresistive element being an integral part of the second flexible member, and wherein the piezoresistive element forms part of a balanced bridge, such as a Wheatstone bridge.

30. The sensor of claim 20 wherein said interaction chamber is between 50 and 500 $\mu M$ in a t least one of width or depth dimensions.

31. The sensor of claim 20 wherein said means for detecting detects a stress change in said first flexible member.

32. The sensor of claim 20 wherein said mechanical parameter sensed by said means for detecting is a static parameter related to stress in said flexible member.

33. A sensor for detecting the presence of a substance in a liquid, said sensor comprising:
    means for handling the liquid, said handling means comprising an interaction chamber of micrometer dimensions, an inlet and an outlet,
    a first flexible member having a surface, said surface holding a substance, wherein the surface holding the substance is at least partly positioned inside the interaction chamber so that at least part of the substance is exposed to the liquid, and wherein the first flexible member forms an integral part of the handling means, and
    means for detecting a mechanical parameter associated with the first flexible member, said mechanical parameter being related to the presence of the substance in a liquid,
    wherein the interaction chamber, inlet and outlet of said means for handling are arranged to establish laminar flow across said first flexible member.

34. A sensor according to claim 33, wherein the first flexible member comprises a cantilever having a first and a second end, wherein the first end is attached to the interaction chamber.

35. A sensor according to claim 33, wherein the detecting means for detecting the mechanical parameter associated with the first flexible member comprises a piezoresistive element, said piezoresistive element being an integral part of the first flexible member.

36. A sensor according to claim 35, wherein the piezoresistive element forms part of a balanced bridge, such as a Wheatstone bridge.

37. A sensor according to claim 33 further comprising an actuator for moving the second end of the cantilever relative to the interaction chamber.

38. A sensor according to claim 37, wherein the actuator comprises a piezoelectric element, said piezoelectric element being an integral part of the cantilever.

39. A sensor according to claim 33, wherein the handling means is fabricated in a material selected from the group consisting of metals, glasses, polymers or semiconductor materials, such as silicon, and wherein the interaction chamber is of micrometer dimensions.

40. A sensor according to claim 33, wherein the substance being held by the surface of the first flexible member is selected from the group consisting of metals, polymers, biochemical molecules or micro-biochemical structures.

41. A sensor according to claim 33, further comprising:
    a second flexible member being at least partly positioned inside the interaction chamber so that at least part of the second flexible member is exposed to the liquid, and
    means for detecting a mechanical parameter associated with the second flexible member.

42. A sensor according to claim 41, wherein the second flexible member detecting means comprises a second piezoresistive element, said second piezoresistive element being an integral part of the second flexible member, and wherein the second piezoresistive element forms part of a balanced bridge, such as a Wheatstone bridge.

43. The sensor of claim 33 wherein said interaction chamber is between 50 and 500 $\mu$M in at least one of width or depth dimensions.

44. The sensor of claim 33 wherein said means for detecting detects a stress change in said first flexible member.

45. The sensor of claim 33 wherein said mechanical parameter sensed by said means for detecting is a static parameter related to stress in said flexible member.

46. A sensor for detecting the presence of a substance in a liquid, said sensor comprising:
    means for handling the liquid, said handling means comprising an interaction chamber of micrometer dimensions, an inlet and an outlet and being fabricated in a material selected from the group consisting of metals, glasses, polymers, or semiconductor materials, such as silicon,
    a first flexible member comprising a cantilever having a first and a second end, wherein the first end is attached to the interaction chamber, said cantilever having a surface, said surface holding a substance, wherein the surface holding the substance is at least partly positioned inside the interaction chamber so that at least part of the substance is exposed to the liquid, and wherein fabrication of the first flexible member is part of fabrication of the handling means,
    means for detecting a mechanical parameter associated with the first flexible member, said mechanical parameter being related to the presence of the substance in the liquid;
    wherein the interaction chamber, inlet and outlet of said means for handling are arranged to establish laminar flow across said first flexible member.

47. A sensor according to claim 46, wherein the detecting means for detecting the mechanical parameter associated with the first flexible member comprises a piezoresistive element, said piezoresistive element being an integral part of the first flexible member.

48. A sensor according to claim 46, further comprising an actuator for moving the second end of the cantilever relative to the interaction chamber.

49. A sensor according to claim 33, wherein the substance being held by the surface of the first flexible member is selected from the group consisting of metals, polymers, biochemical molecules or micro-biochemical structures.

50. A sensor according to claim 46, further comprising:
    a second flexible member being at least partly positioned inside the interaction chamber so that at least part of the second flexible member is exposed to the liquid, and
    means for detecting a mechanical parameter associated with the second flexible member.

51. A sensor according to claim 50, wherein the detecting means comprises a piezoresistive element, said piezoresistive element being an integral part of the second flexible member, and wherein the piezoresistive element forms part of a balanced bridge, such as a Wheatstone bridge.

52. The sensor of claim 46 wherein said interaction chamber is between 50 and 500 $\mu$M in at least one of width or depth dimensions.

53. The sensor of claim 46 wherein said mechanical parameter sensed by said means for detecting is a static parameter related to stress in said flexible member.

54. A sensor for detecting the presence of a first and a second substance in a liquid, said sensor comprising:
    means for handling the liquid, said handling means comprising an interaction chamber of micrometer dimensions, an inlet and an outlet,
    a first flexible member having a surface, said surface holding a first substance, wherein the surface holding the first substance is at least partly positioned inside the interaction chamber so that at least part of the first substance is exposed to the liquid, a second flexible member having a surface, said surface holding a second substance, wherein the surface holding the second substance is at least partly positioned inside the interaction chamber so that at least part of the second substance is exposed to the liquid, a first detecting means for detecting a first mechanical parameter associated with the first flexible member, said first mechanical parameter being related to the presence of the first substance in the liquid, and a second detecting means for detecting a second mechanical parameter associated with the second flexible member, said second mechanical parameter being related to the presence of the second substance in the liquid;

wherein the interaction chamber, inlet and outlet of said means for handling are arranged to establish laminar flow across said first and second flexible members.

55. A sensor according to claim 54, wherein each of the first and second flexible members comprises a cantilever having a first and a second end, wherein the first end is attached to the interaction chamber.

56. A sensor according to claim 54, wherein each of the first and second flexible members comprises a bridge having a first and a second end, wherein the first and second ends are attached to the interaction chamber.

57. A sensor according to claim 54, wherein each of the first and second flexible members forms part of a boundary defining the interaction chamber.

58. A sensor according to claim 54, wherein the first detecting means comprises a piezoresistive element, said piezoresistive element being an integral part of the first flexible member.

59. A sensor according to claim 54, wherein the second detecting means comprises a piezoresistive element, said piezoresistive element being an integral part of the second flexible member.

60. A sensor according to claim 58, wherein each of the piezoresistive elements forms part of a balanced bridge, such as a Wheatstone bridge.

61. A sensor according to claim 54 further comprising actuators for moving the first and second flexible members relative to the interaction chamber.

62. A sensor according to claim 61, wherein the actuators comprise piezoelectric elements, said piezoelectric elements being an integral part of the cantilevers.

63. A sensor according to claim 61, wherein the actuators comprise means for providing an electrostatic induced movement of the second end of the cantilevers.

64. A sensor according to claim 61, wherein the actuators comprise means for providing a magnetic induced movement of the second end of the cantilevers.

65. A sensor according to claim 61, wherein the actuators comprise means for providing a thermal induced movement of the second end of the cantilevers.

66. A sensor according to claim 54, wherein the handling means is fabricated in a material selected from the group consisting of metals, glasses, polymers or semiconductor materials, such as silicon.

67. A sensor according to claim 54, wherein the substances being held by the surface of the first and second flexible members are selected from the group consisting of metals, polymers, biochemical molecules or micro-biochemical structures.

68. The sensor of claim 54 wherein said interaction chamber is between 50 and 500 $\mu$M in at least one of width or depth dimensions.

69. The sensor of claim 54 wherein said means for detecting detects a stress change in at least one of said first and second flexible members.

70. The sensor of claim 54 wherein said mechanical parameter sensed by said first and second detecting means are a static parameters related to stress in said first and second flexible members.

71. A sensor for detecting the presence of a first and a second substrate in a moving laminated liquid, said laminated fluid comprising, in a cross section perpendicular to a direction of movement, a first and a second region, said sensor in comprising:

means for handling the laminated liquid, said handling means comprising an interaction chamber, an inlet and an outlet, wherein the interaction chamber, inlet and outlet of said means for handling are arranged to establish laminar flow of the moving laminated liquid including said first and second regions;

a first flexible member having a surface, said surface holding a first substance, wherein the surface holding the first substance is at least partly positioned inside the interaction chamber so that at least part of the first substance is exposed to the first region of the laminated liquid, a second flexible member having a surface, said surface holding a second substance, wherein the surface holding the second substance is at least partly positioned inside the interaction chamber so that at least part of the second substance is exposed to the second region of the laminated liquid, means for detecting a first mechanical parameter associated with the first flexible member, said first mechanical parameter being related to the presence of the first substance in the first region of the liquid, and means for detecting a second mechanical parameter associated with the second flexible member, said second mechanical parameter being related to the presence of the second substance in the second region of the liquid.

72. A sensor according to claim 71, wherein the detecting means for detecting the first mechanical parameter associated with the first flexible member comprises a piezoresistive element, said piezoresistive element being an integral part of the first flexible member.

73. A sensor according to claim 72, wherein the detecting means for detecting the second mechanical parameter associated with the second flexible member comprises a piezoresistive element, said piezoresistive element being an integral part of the second flexible member.

74. A sensor according to claim 71, wherein the detecting means for detecting the first and second mechanical parameters associated with the first and second flexible member, respectively, comprises a laser, an optical element and a position sensitive photo detector.

75. A sensor according to claim 71, further comprising a first actuator for moving part of the first flexible element relative to the handling means.

76. A sensor according to claim 75, wherein the first actuator comprises a piezoelectric element, said piezoelectric element being an integral part of the first flexible member.

77. A sensor according to claim 71, further comprising a second actuator for moving part of the second flexible element relative to the handling means.

78. A sensor according to claim 77, wherein the second actuator comprises a piezoelectric element, said piezoelectric element being an integral part of the second flexible member.

79. A sensor according to claim 71, wherein the handling means is fabricated in a material selected from the group consisting of metals, glasses, polymers or semiconductor materials, such as silicon.

80. A sensor according to claim 71, wherein the substances being held by the surface of the first and second flexible members are selected from the group consisting of metals, polymers, biochemical molecules or microbiochemical structures.

81. The sensor of claim 71 wherein said interaction chamber is between 50 and 500 $\mu$M in at least one of width or depth dimensions.

82. The sensor of claim 71 wherein said means for detecting detects a stress change in at least one of said first and second flexible members.

83. The sensor of claim 71 wherein said mechanical parameter sensed by said means for detecting first and second mechanical parameters are static parameters related to stress in said first and second flexible members.

84. The sensor of claim 83 wherein first and second fluid regions are introduced into said interaction chamber and maintained separate from each other by the laminar flow therein; said first and second flexible members are each disposed in one of said first and second laminar fluid flow regions.

85. The sensor of claim 71 wherein said first and second mechanical parameters are static parameters.

86. A method for detecting the presence of a substance in a liquid using a sensor including, an interaction chamber of micrometer dimensions having an inlet and an outlet through which a liquid to be sensed is supplied, and at least one cantilevered sensor having a first flexible member provided with a surface reacting to the presence of a substance to be measured, said first flexible member being provided at least partially within said interaction chamber, the method comprising:

introducing the liquid to be sampled to the interaction camber via the inlet and outlet of said interaction chamber so that a laminar flow is established across said first flexible member;

detecting a static mechanical parameter associated with said first flexible member related to the presence of the substance to be measured; and correlating said mechanical parameter to the presence of the substance.

87. The method of claim 53 wherein said static mechanical parameter is a stress change in the first flexible member.

88. The sensor of claim 46 wherein said means for detecting detects a stress change in said first flexible member.

\* \* \* \* \*